United States Patent [19]

Goodman et al.

[11] Patent Number: 5,460,182

[45] Date of Patent: Oct. 24, 1995

[54] TISSUE PENETRATING APPARATUS AND METHODS

[75] Inventors: David E. Goodman, Brookline, Mass.; Daniel S. Goldberger, Boulder, Colo.

[73] Assignee: Sextant Medical Corporation, Boulder, Colo.

[21] Appl. No.: 944,516

[22] Filed: Sep. 14, 1992

[51] Int. Cl.$^6$ ............................................. A61B 6/00
[52] U.S. Cl. ..................... 128/664; 128/665; 128/633; 128/634; 606/2; 607/88
[58] Field of Search ...................... 128/664, 665, 128/754, 633, 634; 606/2, 14, 15, 167, 172, 173; 356/432, 433, 435; 607/88, 89

[56] References Cited

U.S. PATENT DOCUMENTS

| | | | |
|---|---|---|---|
| 2,437,916 | 3/1948 | Greenwald | 128/2 |
| 3,674,008 | 7/1972 | Johnson | 128/2 A |
| 3,847,483 | 11/1974 | Shaw et al. | 356/41 |
| 3,941,121 | 3/1976 | Olinger et al. | 128/6 |
| 3,961,621 | 6/1976 | Northeved | 128/2 B |
| 3,963,019 | 6/1976 | Quandt | 128/2 T |
| 4,191,191 | 3/1980 | Auburn | 128/347 |
| 4,269,192 | 5/1981 | Matsuo | 128/665 |
| 4,290,433 | 9/1981 | Alfano | 128/665 |
| 4,295,470 | 10/1981 | Shaw et al. | 128/634 |
| 4,299,230 | 11/1981 | Kubota | 128/630 |
| 4,311,138 | 1/1982 | Sugarman | 128/214.4 |
| 4,322,164 | 3/1982 | Shaw et al. | 356/243 |
| 4,356,826 | 11/1982 | Kubota | 128/630 |

(List continued on next page.)

FOREIGN PATENT DOCUMENTS 0017108  10/1992  WIPO .................... 128/634

OTHER PUBLICATIONS

Edholm et al., "Tissue Identification During Needle Puncture By Reflection Spectrophotometry", Med & Biol Engng, vol. 6, pp. 409–413 (1968).

Talamini et al., "Laparoscopic Equipment and Instrumentation", Chapter 2, Surgical Laparoscopy (Zucker ed), (1991) pp. 23–27, 35–36, 40–55.

"Instrumentation" Laparoscopic Complication (1991) pp. 5–13.

Edholm et al. "Detection of Aortic Atheromatosis In Vivo By Reflection Spectrophotometry" J.Atheroscler. Res. 5, (1965) pp. 592–595.

Polanyi "In Vivo Oximeter With Fast Dynamic Response", The Review of Scientific Instruments, vol. 33, No. 10, 1962, pp. 1050–1054.

*Primary Examiner*—William E. Kamm
*Assistant Examiner*—Brian L. Casler
*Attorney, Agent, or Firm*—Davis Hoxie Faithfull & Hapgood

[57] ABSTRACT

A tissue penetrating apparatus including a surgical appliance having a sharp tip for penetrating tissue, a first optical element for emitting one or more selected monochromatic wavelengths of light, and a second optical element for sensing light corresponding to the one or more selected monochromatic wavelengths of light. The first and second optical elements are optical transmission fibers secured to the appliance proximate to the tip so that one fiber passes one or more monochromatic wavelengths of light into the tissue to be penetrated, and the other fiber passes the light sensed to a light detector. A control circuit is used to illuminate the one or more light sources to emit light out one of the first and second optical fibers, and to provide an electrical signal corresponding to the light sensed at the other of the first and second optical fibers. The electrical signal includes sensed light at each of the monochromatic wavelengths of light emitted, and sensed light in the absence of emitted light. An analysis circuit or a microprocessor based device may be used for processing the electrical signals and determining when the appliance tip has entered a body cavity. An annunciator is actuated to indicate the relative extent of passage through the tissue and when penetration has occurred.

61 Claims, 15 Drawing Sheets

U.S. PATENT DOCUMENTS

| | | | |
|---|---|---|---|
| 4,410,020 | 10/1983 | Lorenz | 141/65 |
| 4,416,285 | 11/1983 | Shaw et al. | 128/634 |
| 4,421,106 | 12/1983 | Uehara | 128/4 |
| 4,448,194 | 5/1984 | DiGiovanni et al. | 128/334 R |
| 4,502,487 | 3/1985 | DuBrucq et al. | 128/665 |
| 4,527,569 | 7/1985 | Kolb | 128/660 |
| 4,532,935 | 8/1985 | Wang | 128/753 |
| 4,539,586 | 9/1985 | Danna et al. | 358/98 |
| 4,566,438 | 1/1986 | Liese et al. | 128/6 |
| 4,601,710 | 7/1986 | Moll | 604/165 |
| 4,617,940 | 10/1986 | Wang | 128/753 |
| 4,622,974 | 11/1986 | Coleman et al. | 128/634 |
| 4,633,885 | 1/1987 | DuBrucq | 128/736 |
| 4,650,327 | 3/1987 | Ogi | 356/243 |
| 4,658,825 | 4/1987 | Hochberg et al. | 128/634 |
| 4,667,229 | 5/1987 | Cooper et al. | 358/9 |
| 4,682,585 | 7/1987 | Hilterbrandt | 128/4 |
| 4,763,662 | 8/1988 | Yokoi | 128/660 |
| 4,864,648 | 9/1989 | Kordts et al. | 455/608 |
| 4,887,606 | 12/1989 | Yock et al. | 128/662.05 |
| 4,902,280 | 2/1990 | Lander | 604/165 |
| 4,911,148 | 3/1990 | Sosnowaki et al. | 128/6 |
| 4,930,516 | 6/1990 | Alfano et al. | 128/665 |
| 4,945,895 | 8/1990 | Takai et al. | 128/6 |
| 4,951,677 | 8/1990 | Crowley et al. | 128/662.06 |
| 4,970,757 | 11/1990 | Heiland et al. | 452/140 |
| 4,972,827 | 11/1990 | Kishi et al. | 128/3 |
| 4,998,527 | 3/1991 | Meyer | 128/6 |
| 5,000,752 | 3/1991 | Hoskin et al. | 606/9 |
| 5,002,557 | 3/1991 | Hasson | 606/191 |
| 5,030,206 | 7/1991 | Lander | 604/164 |
| 5,030,207 | 7/1991 | Mersch et al. | 604/168 |
| 5,037,433 | 8/1991 | Wilk et al. | 606/139 |
| 5,053,016 | 10/1991 | Lander | 604/169 |
| 5,066,288 | 11/1991 | Deniega et al. | 604/274 |
| 5,078,712 | 1/1992 | Easley et al. | 606/16 |
| 5,104,382 | 4/1992 | Brikerhoff et al. | 604/165 |
| 5,104,383 | 4/1992 | Shichman | 606/167 |
| 5,114,407 | 5/1992 | Burbank | 604/164 |
| 5,116,353 | 5/1992 | Green | 606/184 |
| 5,131,398 | 7/1992 | Alfano et al. | 128/665 |
| 5,139,025 | 8/1992 | Lewis et al. | 128/665 |
| 5,140,989 | 8/1992 | Lewis et al. | 128/665 |
| 5,152,278 | 10/1992 | Clayman | 128/4 |
| 5,219,345 | 6/1993 | Potter | 128/665 |
| 5,271,380 | 12/1993 | Riek et al. | 128/4 |
| 5,280,788 | 1/1994 | Janes et al. | 128/665 |
| 5,318,023 | 6/1994 | Vari et al. | 128/634 |
| 5,350,148 | 9/1982 | Sivak, Jr. et al. | 128/4 |

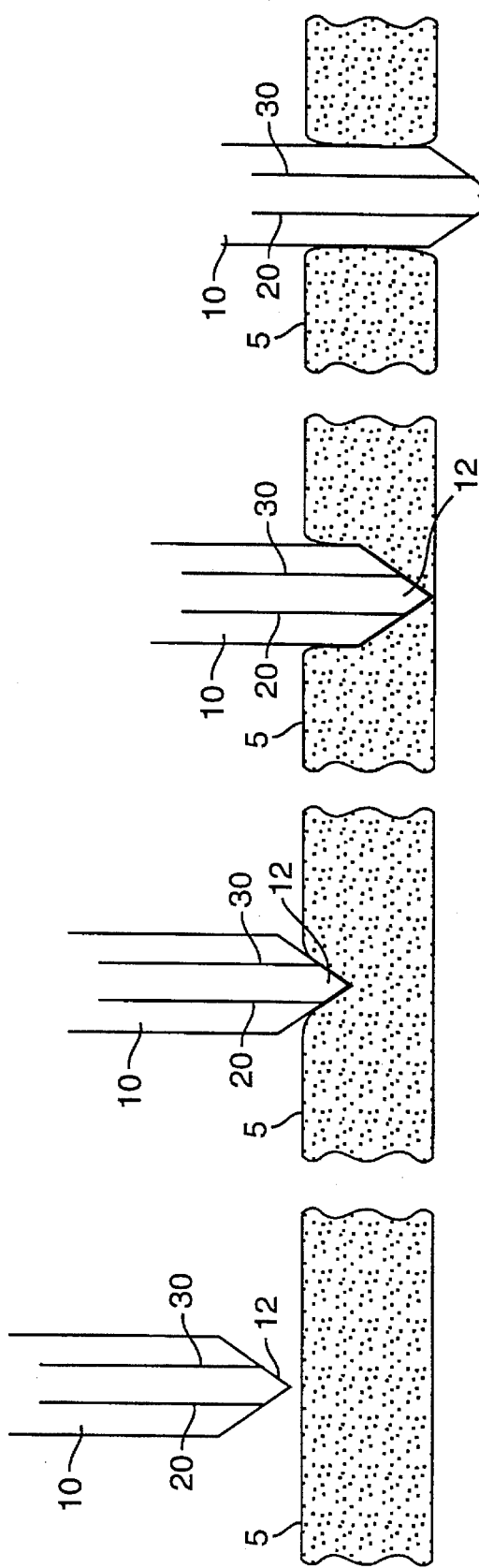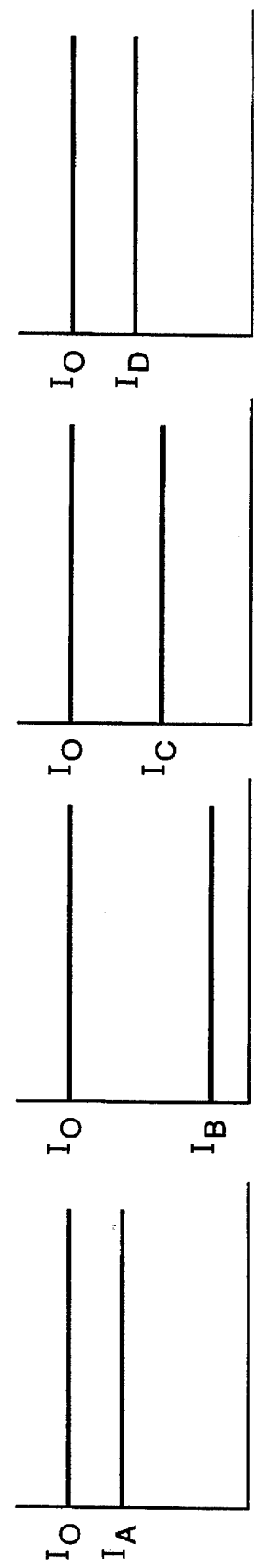

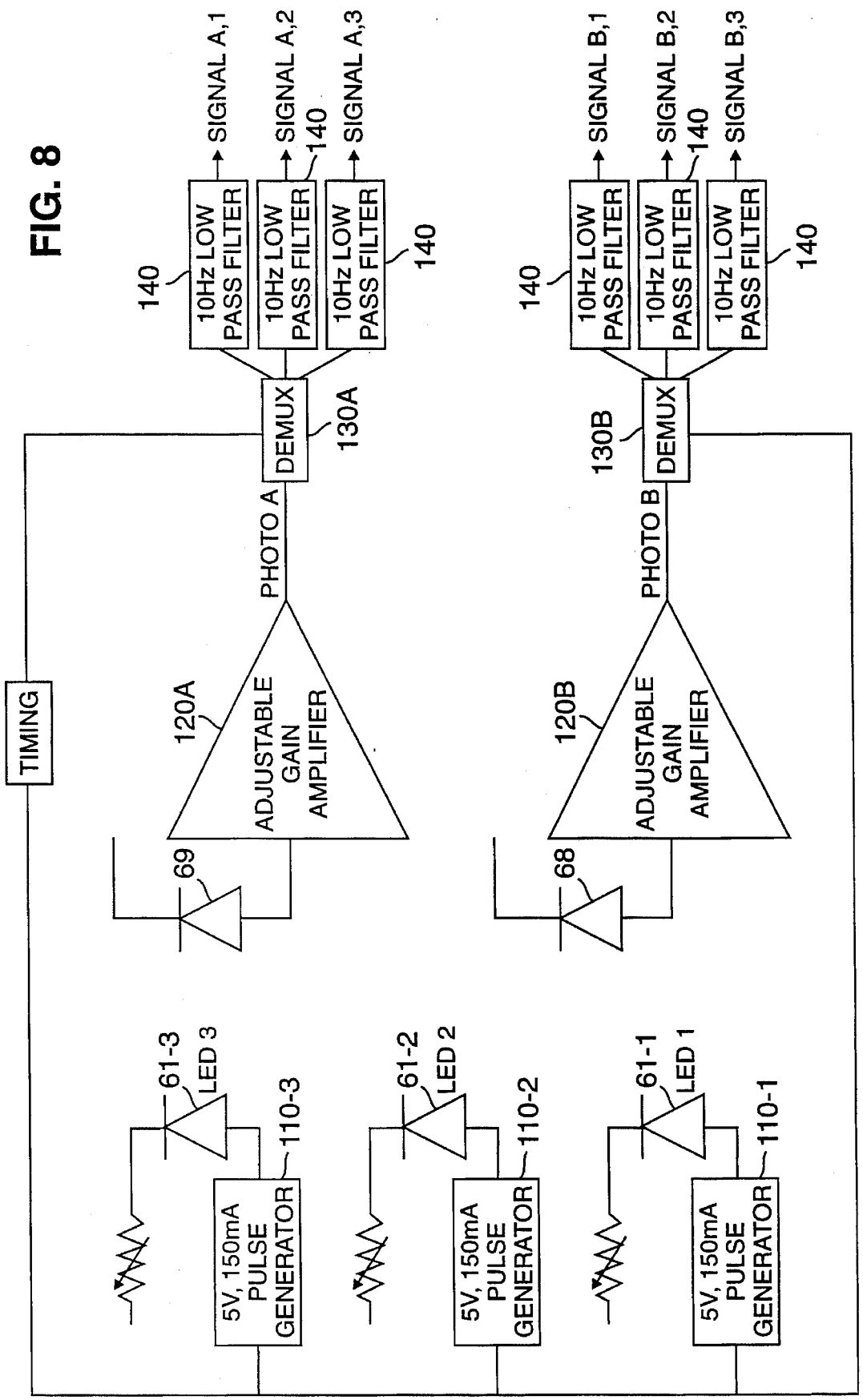

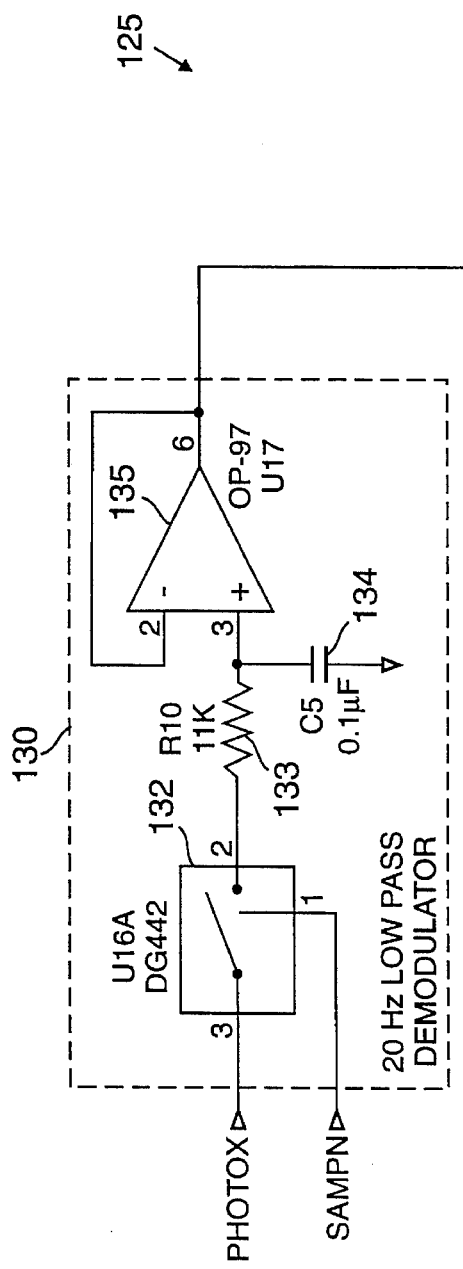
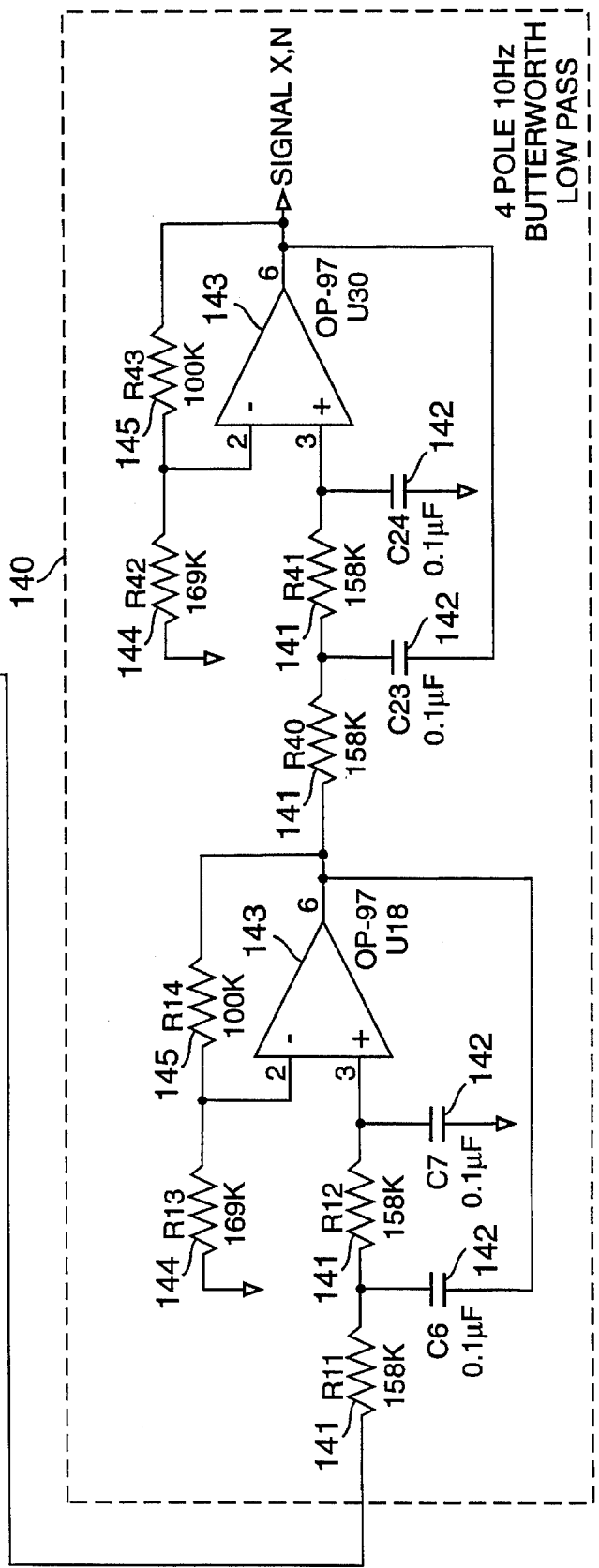
FIG. 13

TISSUE PENETRATING APPARATUS AND METHODS

FIELD OF THE INVENTION

This invention relates to penetrating tissue and more particularly to a trocar or surgical needle for accurately and safely penetrating tissue into a body cavity in connection with minimally invasive surgical procedures.

BACKGROUND OF THE INVENTION

The field of minimally invasive surgery, including without limitation laparoscopic and endoscopic surgery, has recently experienced dramatic growth. Procedures such as laparoscopic appendectomy and cholecystectomy (removal of the gall bladder), and various gynecological procedures have become widely adopted in clinical practice. When performed safely, the minimally invasive alternatives to traditional surgical intervention can reduce costs of care by shortening hospital stays and recuperation times. They also provide collateral benefits such as reduced patient discomfort and better cosmetic results, i.e., reduced scarring. There is strong demand being generated by patients for these alternate procedures.

Minimally invasive procedures frequently begin with obtaining access to a body cavity, for example, the abdomen, through the use of specialized trocars and surgical needles. Typically, for one example, a laparoscopic procedure begins with the insertion of a specialized insufflation needle, commonly known as a Verres needle, into the abdominal cavity. Once inserted, carbon dioxide is introduced through the needle (insufflation) to create what is called a pneumoperitoneum. This distends the abdominal wall to separate it from the underlying vital organs. The pneumoperitoneum is designed to protect the abdominal contents during insertion of the trocar.

The next step is to establish one or more portals through which various diagnostic and/or operating instruments can be inserted and, once inside the body, manipulated to perform the desired function. Devices for creating such portals are commonly known as trocars, which include a puncturing tool having a sharp tip that is pressed into and through the tissue, and a hollow sleeve or cannula. The puncturing tool and sleeve are forced into the skin and through the tissue in combination. Once the tool has punctured the tissue and passed into the body cavity, it is removed, leaving the sleeve as a rigid conduit forming the portal. The puncturing tool tip is commonly known as a trocar tip, which is secured to the end of a structure called a sheath or an obturator or obturator tube.

Typically, a rigid laparoscope is the first instrument inserted into the body cavity through the established portal. The laparoscope provides for direct visualization of the body cavity. A miniature video camera is commonly attached to the laparoscope eyepiece so all subsequent procedures can be easily viewed on a video screen (CRT). Other portals may be created in a similar fashion for the insertion of additional instruments having diagnostic and/or surgical functions.

In addition to laparoscopic surgery, there are other indications for penetrating a body cavity with a trocar or other puncturing tool such as a surgical needle. Examples include paracentesis and thoracentesis whereby a needle is inserted into the abdominal or thoracic cavity for the purpose of withdrawing collections of fluid which may be abnormal.

One problem with insertion of the Verres needle, trocar, and similar puncturing tools is that the initial puncture (insertion) is performed blind. Thus, it can be difficult to tell with certainty that the needle or trocar tip has entered the desired body cavity. This can lead to a variety of complications such as inadvertent insufflation of extraperitoneal tissues with $CO_2$. If this occurs, the patient may experience subcutaneous emphysema (gas in the tissues under the skin) or even lethal hypercarbia (high levels of $CO_2$ in the blood).

Other complications include punctured abdominal viscus (e.g., bowel) or vascular injury (e.g., aorta). Although relatively rare, these complications carry significant morbidity and mortality. This is especially problematic as laparoscopic and other minimally invasive surgical procedures are increasingly performed out of the hospital environment where sophisticated emergency backup may not be readily available. Although ultrasound or fluoroscope techniques may be of some assistance, they are difficult to use, add complexity to the procedure and require additional, expensive equipment and personnel trained to operate the equipment.

Devices to enhance the safety of trocar insertion are known. For example, U.S. Pat. Nos. 5,114,407, 5,104,382, 5,116,353, 4,601,710 and 5,066,288 refer to safety trocars having either spring-loaded shields or self-retracting trocar tips either to cover or remove the sharp tip of the trocar after it penetrates a body cavity and prevent inadvertent tissue injury. The safety mechanisms are typically cocked prior to use and designed to engage after a loss of tissue resistance occurs, such as that which usually occurs when a body cavity is entered. Loss of tissue resistance may be sensed, for example, by loading on a spring release mechanism.

These devices suffer from several drawbacks. First, the safety mechanisms can operate to obstruct the trocar tip before it actually (or fully) penetrates the tissue into the body cavity. Conversely, the mechanisms may fail to engage after the body cavity is entered such that relying upon the engagement of such devices as an indicator of penetration may result in erroneously continuing to advance the sharp trocar.

U.S. Pat. No. 4,191,191 refers to a laparoscopic trocar with a screw mechanism to effect gradual penetration into the abdominal cavity. One disadvantage of this device is that no mechanism is provided for ensuring that the trocar has actually entered the abdominal cavity.

SUMMARY OF THE INVENTION

It is an object of the present invention to provide a tissue penetrating device that provides for safe and accurate penetration of a body cavity and overcomes the deficiencies of the prior known techniques.

It is a further object of the invention to provide a tissue penetrating device with an optical sensor for use in determining whether or not the penetrating device has penetrated the desired body cavity. It is another object to provide a puncturing tool such as a trocar or surgical insufflation needle with such an optical sensor. It is another object to provide an optical sensor having a multiplicity of optical components at the distal end of the puncturing tool for emitting light and sensing reflected light to provide a signal corresponding to when the tool has penetrated the desired body cavity.

It is another object to provide a circuit for processing sensed reflected light signals for determining when a puncturing tool enters a body cavity. It is another object to generate an alarm when penetration has occurred. It is another object to determine when the tissue penetrating device is about to pass through the body cavity into underlying tissue or organs. It is another object of the invention to generate an alarm when penetration is about to occur.

In accordance with a first aspect of the invention, a tissue penetrating device is provided with a puncturing tool having a sharp tip for penetrating body tissue, a light emitting element secured to the tip for emitting radiation at one or more selected wavelengths into the tissue to be penetrated, and a light detecting element secured to the tip for coupling the light intensity corresponding to at least the emitted wavelength(s). Preferably, the light detecting element senses the light intensity at the tissue when the tissue is illuminated by one or more selected wavelengths, which light intensity is related to the relative proportion of the incident light that is reflected from and/or absorbed by the tissue (hereinafter referred to as the "light illumination"). These sensed light illuminations provide for determining the net change in reflection and/or absorption in one or more of the emitted wavelengths as the device tip moves into and through the tissue. More preferably, the light detecting element also senses the intensity of light during ambient light conditions when the tissue is not so illuminated (hereinafter referred to as the "dark illumination"). The sensed dark illumination is used to remove the ambient light component from the sensed light illumination to identify changes unrelated to changes in ambient conditions.

It should be understood that the light emitting element of the light detecting element may be arranged in any configuration on the tip so that, in response to the light intensity launched by the light emitting element, the light detecting element produces a signal that changes detectably as the light detecting element passes from being in the tissue to being in the body cavity. In this regard, the light emitting and detecting elements may be oriented in either (1) transmissive line of sight, wherein there is a line of sight light path between the light emitting element and the light detecting element and the presence of tissue reduces the intensity of light illumination sensed by the detecting element, (2) transmissive over the horizon, wherein there is no direct line of sight light path between the light emitting and detecting elements, the presence of tissue couples light to the light detecting element, and the absence of tissue reduces the intensity of light illumination coupled to the light detecting element, (3) reflective over the horizon, wherein there is no direct line of sight light path between the light detecting and light emitting element, the presence of tissue attenuates the light intensity sensed at the light detecting element and the absence of tissue results in an increased light intensity sensed at the light detecting element, or (4) some combination thereof.

The aforementioned signal change is preferably a change in amplitude, but may be a modulation of a carrier frequency, a phase shift, or change in some other signal parameter.

The light illumination sensed by the detecting element may be one or more of the selected wavelengths launched by the light emitting element. In addition, the light detecting element may be selected to detect wavelengths corresponding to tissue fluorescence when the tissue is illuminated with appropriate wavelengths of light. The use of fluorescence may be in place of or in addition to sensed changed in intensity of the light wavelength(s) launched by the light emitting element. Accordingly, as used herein, references to monitoring light intensity should be understood to include both the intensity of launched wavelength and the intensity of other wavelengths in response to launched wavelengths when desired or conditions permit.

The light emitting and detecting elements are coupled to a circuit for driving the light emitting element and a circuit for monitoring the light intensity sensed by the light detecting element. The monitoring circuit also may process the detected light intensity signals to identify a selected change in the sensed light intensity corresponding to the device tip passing into and through the tissue. The light driving and monitoring circuits are preferably operated so that the light illumination in response to each emitted wavelength is separately determined.

The light emitting element may be a device for emitting radiation, and the light detecting element may be a device that produces an electrical signal in response to the light intensity sensed at one or more desired wavelength(s). More preferably, the light emitting element is a length of an optical waveguide or light transmission fiber (hereinafter referred to as an "optical fiber" or "optical waveguide"). The optical fiber conducts light, including the one or more selected and desired wavelengths, e.g., from a light receiving end to a light emitting end. The light emitting end is in the device tip and launches light into the tissue being or to be penetrated or into the body cavity following penetration. More preferably also, the light detecting element is an optical fiber for coupling light at its receiving end to a light emitting end remote from the tissue. The light receiving end is in the device tip and senses the light intensity at the tissue being or to be penetrated or in the body cavity following penetration. In the latter preferred embodiments, the optical fiber light emitting element is coupled at its light receiving end to the driving circuit, and the driving circuit includes a light source providing the one or more selected wavelengths. Preferably, the selected wavelengths are monochromatic. Similarly, the light emitting end of the optical fiber light detecting element is coupled to the monitoring circuit, and the monitoring circuit includes a light detector which produces an electrical signal corresponding to the intensity of the desired coupled wavelength(s).

When multiple discrete wavelengths of light are used as the selected wavelengths launched and the desired wavelengths sensed, they may be multiplexed by frequency or by time for transmission to the tissue on a common optical waveguide. This permits using a single optical fiber, having a very small diameter, as the light emitting element. Alternately, the discrete wavelengths may be separately delivered over corresponding dedicated optical waveguides. Further, more than one optical waveguide may be used to deliver the same wavelength(s) simultaneously at different points on the device tip.

Similarly, the light detecting element may be one optical waveguide adapted to receive all light sensed, which detected light signal can be optically (frequency) or electrically (time) demultiplexed and separated into different sensed light intensity signals corresponding to the different desired wavelengths. Alternately, the light detecting element may have separate optical waveguides for receiving the light and either selectively passing one discrete wavelength to a light detector or passing the light to a wavelength selection light detector, for generating the separate corresponding electrical signals. Further, the light detecting element may have more than one optical waveguide to detect the light such that the detected light signals are averaged, summed, or otherwise related to yield a detected light level for each emitted frequency.

Another aspect of the present invention is directed to a circuit for analyzing the sensed light illumination at the tissue to identify changes in the sensed light intensity corresponding to the device tip passing into a selected body cavity. The analyzing circuit preferably processes more than one wavelength separately. This is so that the changes in reflection by and absorption in the tissue for each 10 desired wavelength light over time, e.g., one or more of the emitted wavelengths and any fluorescence wavelengths, can be evaluated individually and/or collectively to provide a reliable indication of the passage of the sharp tip through the tissue and into the cavity. Preferably, the analyzing circuit obtains and processes light illumination and dark illumination samples obtained close in time to remove the effects of changes in dark illumination over time from the determined changes in light intensity at the tissue.

Another aspect of the present invention is directed to analyzing the sensed light illumination changes of tissue for periodic changes in light intensity corresponding to the pulsatile flow of blood. Pulsatile changes in light intensity will suddenly cease when the light-emitting tip is no longer in intimate (touching) contact with blood perfused tissue, such as occurs when the tip penetrates a body cavity.

It is another aspect of the present invention to convert the sudden change in light intensity and/or the loss of periodic change of intensity into an easy to interpret indicator of body cavity penetration for the operator. This indicator, which may be an audible, visual, or tactile signal (or some combination thereof), enables the operator to respond to penetration and cease advancing the sharp tissue penetrating device. It also enables the operator to respond to an indication that the tip is close to penetrating the cavity and either reduce the pressure used to press the tip into the tissue, or reduce the distance the tip is incrementally advanced, e.g., by a conventional ratchet-type or screw (helical) advancing mechanism when one is used, as are described in the aforementioned patents.

Preferably, the light emitting and detecting elements comprise a plurality of optical components, such as optical fibers, at the device tip which are plugged into and thus coupled to an optical bench containing the light source(s) and the light detector(s) such as photodiodes, phototransistors, photomultiplier tubes, charge coupled devices, and the like. Such optical fibers can be made of glass or plastic materials for reusable and disposable device tips. Glass fibers are preferred for reusable tips and plastic fibers are preferred for disposable tips. The optical bench can be made in a durable case and reused for both disposable and reusable device tips. The optical fibers may be identical in construction and symmetrically secured in or to the tissue penetrating device tip so that either fiber (or group of fibers) may be used either to illuminate tissue or to sense light from the tissue.

Advantageously, the present invention provides for a tissue penetrating device having optical elements and control circuits that can be used to determine reliably and accurately when the tissue penetrating device has penetrated a layer of tissue and passed into a desired body cavity. It also provides for disposable components for trocars or surgical insufflation needles containing inexpensive optical elements to insure optimal performance of the invention and prevention of cross-contamination between patients. Alternately, the invention provides durable trocars and insufflation needles with optical elements that will withstand sterilization by autoclave, gas, and x-ray sterilization techniques.

Also advantageously, the present invention can be used to modify the known safety trocar devices to extend a safety shield or retract the trocar tip into a cavity when the optical sensor, rather than the force sensing mechanism, indicates that adequate body cavity penetration has occurred. The present invention also provides for modifying the known safety trocar devices by activating a motor or other electronic actuator, such as an electromagnet or solenoid, in response to an optical signal, to drive positively the shield relative to the trocar tip into the safety position. Thus, the present invention replaces the less consistent springs and frictional contact used in the known devices with precise, powered devices that are more reliable and less prone to both premature and belated release.

BRIEF DESCRIPTION OF THE DRAWINGS

Further features of the invention, its nature and various advantages will be more apparent from the drawings and the following detailed description of the invention, in which like reference numerals refer to like elements, and in which:

FIGS. 2A–2D are a sequence of steps illustrating a process of passing the tissue penetrating device of FIG. 1 through tissue;

FIGS. 2E–2H are plots of relative sensed light intensity corresponding to the devices of FIGS. 2A–2D, respectively;

FIG. 6 is a timing diagram for operating the system of

FIG. 5;

FIG. 8 is a block diagram of the control circuit for the system of FIG. 5;

FIG. 13 is a schematic circuit diagram of the analog circuit for the demultiplexer and low pass filter of FIG. 8;

DETAILED DESCRIPTION OF THE INVENTION

Figure 1:
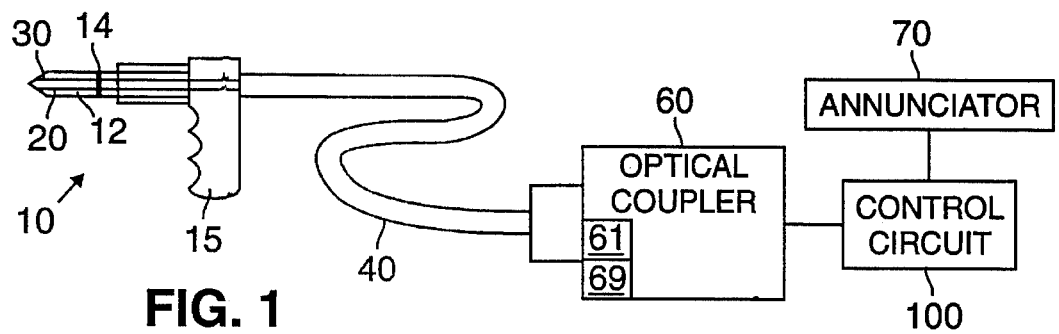
FIG. 1 is a block diagram of a system for a tissue penetrating device in accordance with a preferred embodiment of the present invention.
Figure 1A:
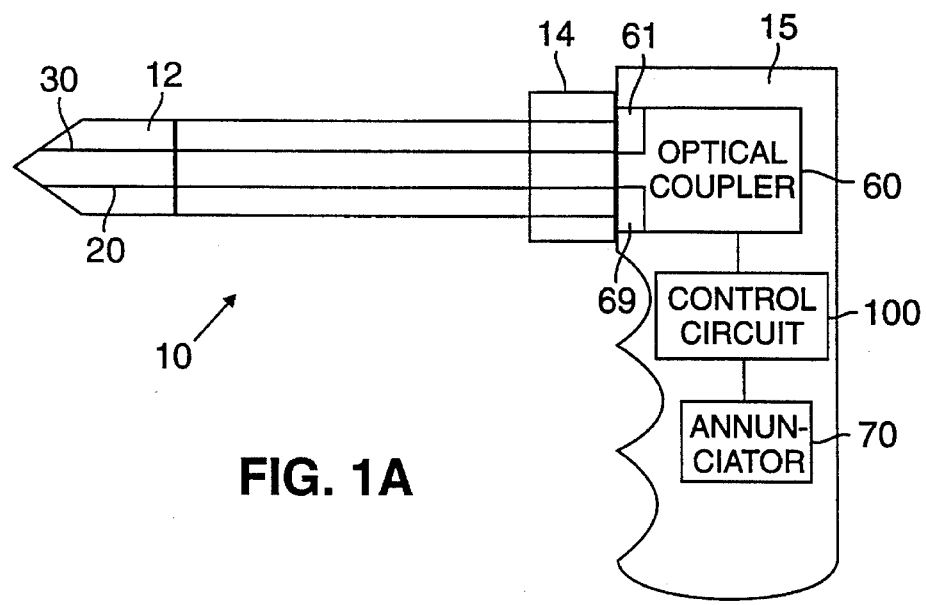
FIGS. 1A and 1B are block diagrams of alternate embodiments of the system of FIG. 1.

Referring to FIGS. 1 and 1A, a tissue penetrating device in accordance with alternative preferred embodiments of the present invention is shown. The device includes a puncturing tool or surgical appliance 10 having a sharp tip 12, a first optical element 20 and a second optical element 30 secured to tip 12, an optical coupler 60, a control circuit 100, and an annunciator 70. The surgical appliance 10 may be any appliance for penetrating tissue such as a trocar, insufflation (Verres) needle, surgical needle or like devices. Any conventional surgical tool may be used, provided that it is modified by the addition of the first optical element 20 and the second optical element 30, as described below.

Optical elements 20 and 30 and optical coupler 60 provide for emitting light at one or more selected wavelengths at the distal tissue contacting end of appliance 10 near tip 12, and for sensing light at the distal end near tip 12. An electrical signal corresponding to the sensed light intensity at tip 12 is then provided by appliance 10. More specifically, coupler 60 contains a light source 61 for providing the one or more selected wavelengths and a light detector 69 for sensing light intensity. Optical elements 20 and 30 couple and transmit light between the source 61 to tip 12 and from tip 12 to light detector 69. For convenience of discussion, optical element 20 is designated to couple light from source 61 and transmit it to the tissue and optical element 30 is designated to couple light sensed at the tissue and transmit it to detector 69.

Control circuit 100 provides the control signals to cause source 61 to emit the one or more wavelengths, and detector 69 to sample the light intensity levels, including the light illumination in response to the emitted one or more wavelengths, at the appropriate times. Control circuit 100 also includes circuits for signal processing of the electrical signals to identify the changes in the sensed light signal, e.g., intensity, at the tissue in response to the one or more incident wavelengths corresponding to tip 12 passing in and through (broaching) the tissue into the body cavity.

As illustrated in FIG. 1A, coupler 60 and control circuit 100 may be physically combined, preferably in a miniaturized package, and incorporated into a body or handle 15 which is used for manipulating appliance 10.

Annunciator 70 may be any sensory device for indicating when control circuit 100 has detected the occurrence of a particular event, e.g., a change in sensed light illumination corresponding to tip 12 of appliance 10 having broached the tissue. Annunciator 70 may generate an audible tone or sequence of tones, illuminate a lamp or LED, or provide a tactile response such as the controlled vibration of a piezoelectric crystal.

Preferably, annunciator 70 is controlled by circuit 100 to provide an audible signal having a variable volume, frequency, tone and/or pitch which changes as the sensed light illumination at tip 12 changes as tip 12 passes through the tissue. In this regard, and with reference to FIGS. 2A-2H, and 14, the sensed light illumination intensity will change (illustrated in this example as an increase) as the optical element 30 moves closer to the distal side of the tissue 5. The intensity level will rise substantially when the tip 12 broaches the tissue on the distal side and the light wavelengths launched into the body cavity by light emitting element 20 are reflected to detecting optical element 30 and not absorbed by tissues. This is illustrated by FIGS. 2A–2H, which show sensed light intensity when tip 12 is outside the proximate side of tissue 5 (FIGS. 2A, 2E), part-way inside tissue 5 (FIGS. 2B, 2F), almost through tissue 5 (FIGS. 2C, 2G) and all the way through tissue 5 past the distal side (FIGS. 2D, 2H). $I_o$ represents the emitted light intensity as may be sensed by a detector 68 (FIG. 5), and $I_A$, $I_B$, $I_C$, and $I_D$ represent the sensed light illumination (preferably corrected for dark illumination) for each of FIGS. 2A–2D respectively. Only one discrete wavelength is shown for clarity. FIGS. 2E–2H are illustrated and not to scale. As used herein, the term "penetrating contact" refers to the sequence of steps generally illustrated in FIGS. 2A–2D.

The audible signal may thus adjust for relative changes in sensed light, corresponding to changes in absorption and/or reflection of the emitted light (or fluorescence in response to the emitted light). Importantly, signal changes may be used to provide the operator with a first clue that penetration will soon occur and a second clue that will confirm that penetration has occurred. The signal range may be adjustable by the operator. Similarly, annunciator 70 may control the intensity of a light source or the number of a scaled array of light sources that are illuminated to provide visually the clue regarding the extent of penetration.

A simple tone generator, which changes the tone, volume, frequency or pitch in response to changes in the intensity of the sensed light, may be used as annunciator 70. In this regard, the light intensity may be the sum or a weighted sum of each wavelength sensed in response to the emitted wavelengths, or of a particular wavelength or combination of wavelengths. The particular combination may vary depending on the tissue type or procedure.

In circumstances where the correlation between sensed light illumination is not sufficiently linear to the penetration of tip 12 through tissue, annunciator 70 is provided with a suitable non-linear response. This provides a variation in the audible, visual or tactile signal that corresponds to the relative penetration of tip 12. Further, the signal to penetration relationship may be made non-linear so that a greater signal variation occurs as the tip about to broach and is broaching the tissue, than occurs as the tip first penetrates the tissue. This provides for easier recognition of the first and second clues.

Figure 1B:
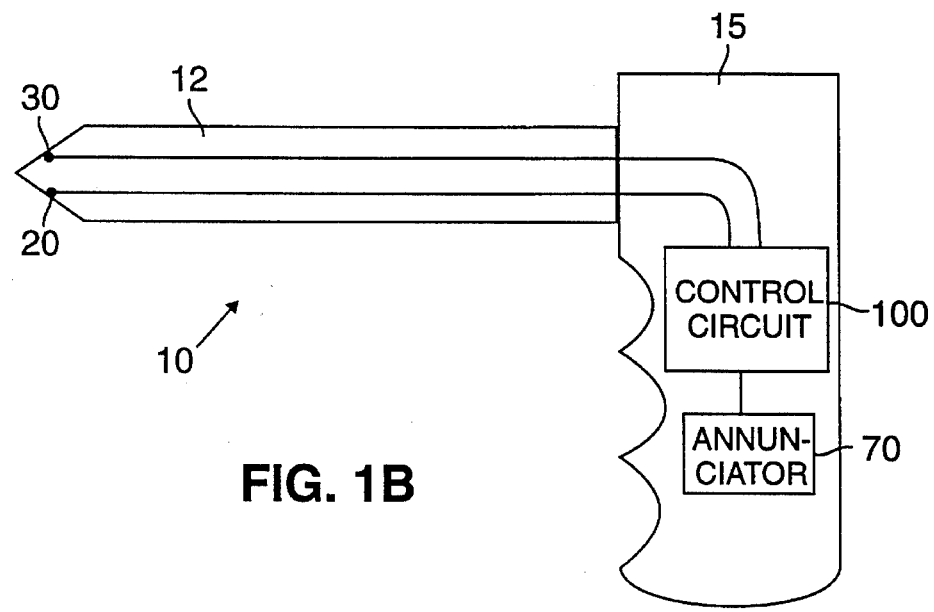

Referring now to FIG. 1B, an alternate embodiment of the present invention is shown wherein optical elements 20 and 30 are the light emitting and light sensing elements respectively. Accordingly, elements 20 and 30 are directly connected to control circuit 100. This embodiment further simplifies construction and operation. Elements 20 may be one or more light emitting devices secured to tip 12, e.g., potted in a receptacle (not shown) using a light transmissive resin potting compound (a low vapor pressure epoxy) or medical grade silicone adhesive and sealant. Similarly, element 30 may be one or more light detecting device potted in tip 12. Although optical coupler 60 may be omitted, it is preferred that some form of electrical isolation be provided between the patient and the control electronics, e.g., opto-electric isolators. This is to prevent injurious signals from passing between the patent and appliance 10. Fiber optics provide the necessary isolation.

Referring now to FIGS. 1, 1A, and 3A–3D, in this embodiment appliance 10 is illustrated as a conventional trocar tip for laparoscopic surgery, which has been modified as described below. The sheath and obturator tubes are not shown. Optical elements 20 and 30 are provided in the form of first and second lengths of optical fibers, and coupler 60 is an optical coupler including a light source 61 for launching one or more of the selected illuminating wavelengths onto one of fibers 20 and 30, e.g., optical fiber 20, and a light detector 69 for sensing light at tip 12 by the other of fibers 20 and 30, e.g., optical fiber 30.

In this embodiment, the conventional surgical trocar appliance 10 (reusable or disposable) is modified by the incorporation of two optical fibers 20 and 30 into or on the structure. Optical fibers 20 and 30 are each a single fiber that is small in diameter and may be of conventional plastic or glass construction. The fiber diameter should be selected to be from between 0.05 and 0.25 mm, so that the mechanical function of the sharp appliance tip 12 is not compromised. Fibers as large as 1.0 mm diameter may be used on large trocar applications, i.e., a trocar having a 10.0 mm diameter. Glass optical fibers have superior optical transmission characteristics and are available in the smaller sizes. Glass optical fibers also have better mechanical and thermal properties, such as the ability to withstand autoclave temperatures. Plastic fibers are much less expensive, which makes them well suited to disposable devices and reusable devices where sterilization by autoclave is not required.

Referring to FIGS. 3A–3D, in this embodiment the optical fibers 20 and 30 are secured to tip 12 by being mounted into small holes formed in the tip 12 near the point of surgical appliance 10 and fixed in place with a medical grade adhesive or potting compound. The exact positions of the ends of fibers 20 and 30 are chosen to minimize the likelihood of a direct optical path between the two, which would allow optical crosstalk. The position of the fiber ends in the cutting faces of tip 12 also are selected so that when the light illumination changes in response to the ends of fibers 20 and 30 passing into the cavity, the puncture in the tissue is sufficiently large that further advance of tip 12 is not required.

A preferred position also is to have the elements 20 and 30 geometrically symmetrical, so that the optical transmission/reception characteristics of fibers 20 and 30 are identical and therefore interchangeable. This permits making coupler 60 a durable component that is plug-compatible with appliance 10 and its tip 12 having secured optical fibers 20 and 30. Alternately, coupler 60 may have a "plug" that is keyed so that a selected optical element 20 or 30 will be used for sensing (or illuminating) light. This is useful when an optical element 20 or 30 on appliance 10, or its manner of mounting or its positioning, is specially designed for light illumination or sensing, but not both.

In addition, appliance 10 and coupler 60 may be constructed with a coding system (not shown) whereby each appliance 10 includes or has associated with it a code that identifies the type of appliance 10, i.e., its surgical purpose and the configuration of optical elements 20 and 30 on tip 12 of that appliance. This code is read by control circuit 100, for example, when appliance 10 is coupled to coupler 60 and/or when the device is turned on. The code is identified and used to select appropriate timing signals and signal levels for controlling the illumination and detection of light, and to select appropriate thresholds for processing the sensed light signals and making determinations regarding tissue penetration. In this embodiment, control circuit 100 may be provided with a memory device (not shown) containing a conventional look-up table or prerecorded information, for providing all of the necessary operating parameters that are associated with a given code. Further, if a code is not recognized, the device may automatically shut down so that incompatible appliances are not incorrectly used. Any method of coding appliances 10 may be used, such as using selected resistor values or digital words in a circuit integral in appliance 10 and corresponding contacts in coupler 60 for electrically sensing the code by circuit 100. In addition, product labeling such as a bar code on appliance 10 and a photodetector array and sensors on coupler 60 may be used for optically sensing the code by circuit 100. Coding optical sensing devices are discussed in, for example, U.S. Pat. Nos. 4,621,643, 4,700,708, and 4,770,179, the disclosures of which are hereby incorporated by reference.

Referring again to FIGS. 3A–3D, one construction of trocar 10 has a tip 12 that includes a 3-face pyramid. The faces are cut on essentially flat planes that intersect at an angle of 120° relative to each other (see angle e in FIG. 3B) and so that the midline of one facet and the edge of an adjacent facet form an angle of 45° (see angle β in FIG. 3C) with the apex being the point of tip 12. This trocar tip construction is conventional.

Figure 3A:
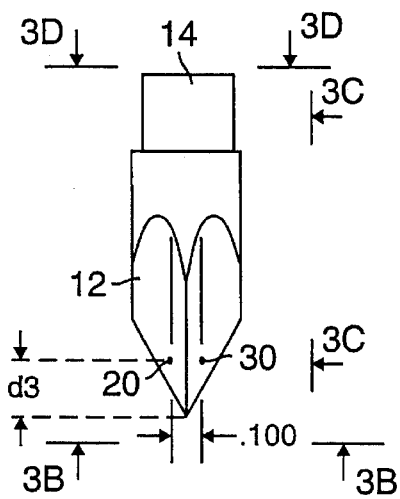
FIG. 3A is a front elevated view of a trocar tip tissue penetrating device in accordance with the present invention.
Figure 3B:
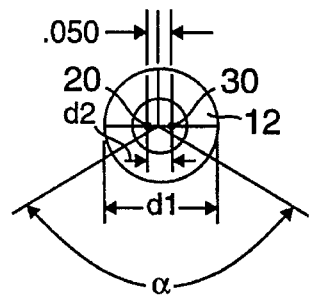
FIG. 3B is a tip end view taken along line 3B—3B of FIG. 3A.
Figure 3C:
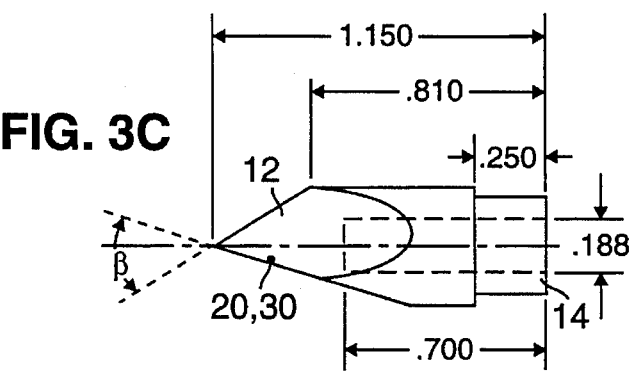
FIG. 3C is a side view taken along line 3C—3C of FIG. 3A.
Figure 3D:
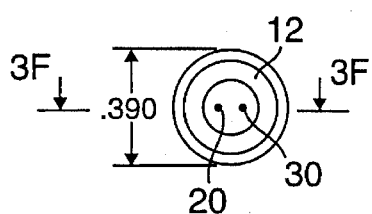
FIG. 3D is a base end view taken along line 3D—3D of FIG. 3A.

For a conventional trocar made of 440 stainless steel having an outer diameter d1 of 0.39 inches, fibers 20 and 30 are respectively inserted into two parallel 0.013-inch-diameter holes, which are spaced apart a distance d2 of 0.1 inches along a diameter of tip 12, and centered about the point of tip 12. In this embodiment, the faces of fibers 20 and 30 are flush with the plane of the facet of trocar 12, and terminate a distance d3 of 0.07 inches from the point of tip 12 as illustrated in FIG. 3A.

The trocar tip 12 may be constructed as follows. Two holes are drilled. The fibers 20 and 30 are coated with silicone adhesive and passed into the drilled holes so that the ends of fibers 20 and 30 extend from the tip faces. The adhesive is allowed to set. The ends of fibers 20 and 30 are then trimmed either separately or during the process for tipping the tip. The fiber ends are then polished. The inside of trocar tip 12 may be partially filled with a potting material to provide additional support for fibers 20 and 30.

Figure 3E:
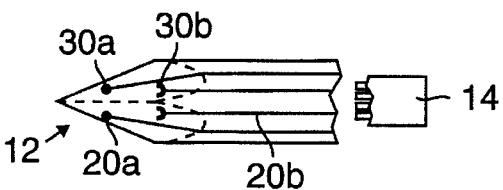
FIGS. 3E–3G and 3L are side views of a trocar tip tissue penetrating device in accordance with different embodiments of the present invention.

Referring to FIG. 3E, an alternative construction of tip 12 is shown. In this embodiment, tip 12 has two pairs of optical elements 20 and 30, namely optical fibers 20a and 30a, and optical fibers 20b and 30b. The placement of the ends of fibers 20b and 30b are selected so that element 30b will sense predominantly light illumination launched by optical element 20b, rather than 20a. In one embodiment, the two pairs are separately operated to provide different signals of light (and dark) illumination corresponding to different sensing locations on tip 12. Pair of fibers 20a and 30a provide the light (and dark) illumination at the point of tip 12 and fibers 20b and 30b provide the light (and dark) illumination closer to the base 14 of tip 12. This provides a first signal which indicates when the leading point of tip 12 has broached the tissue, and a second signal which indicates when the full diameter of the base of tip 12 has broached the tissue. Advantageously, the annunciator 70 can be configured to alter the signal accordingly. This provides alarms so that the surgeon can respond to a first alarm when the point broaches and ease up on the pressure, and respond to a second alarm when the puncture is complete and withdraw the tip 12. Importantly, a third alarm may be generated if the point of tip 12 subsequently reenters tissue inside the body cavity (or comes in sufficiently close proximity) to alert the surgeon of a possible complication that otherwise might go unnoticed.

In a second embodiment, the pairs of optical elements in FIG. 3E may be connected so that optical elements 20a and 20b are coupled to a common light source 61 and optical elements 30a and 30b are coupled to a common light detector 69 (not shown). Thus, with light source 61 maintained at a relatively constant illumination level, the light illumination intensity sensed by detector 69 will have a multilevel light intensity signal corresponding to (1) both pairs being out of the tissue (prior to penetration), (2) one pair being in the tissue at the penetration and the other pair being out of the tissue prior to penetration, (3) both pairs being in the tissue, (4) one pair being in the body cavity and the other pair being in the tissue, and (5) both pairs being in the body cavity. Accordingly, annunciator 70 may be configured to generate different signals corresponding to the different signal levels.

The control circuit 100 described below may be easily modified to accommodate two or more pairs of optical elements.

Figure 3F:
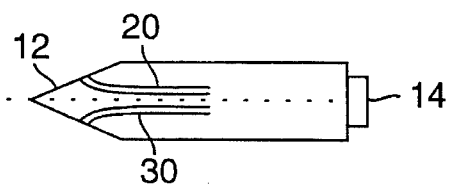
Figure 3G:
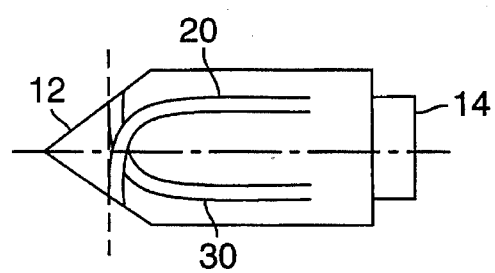

In alternate embodiments, the optical elements 20 and 30 may be constructed to terminate with their ends normal to the tissue contacting surface (see FIG. 3F) perpendicular to the longitudinal axis (see FIG. 3G), or various other angles or combinations of angles, taking into consideration the allowable radius of curvature of the optical fibers.

Referring to FIGS. 3H–3K, an alternate embodiment of a disposable appliance 10 having a conial-shaped trocar tip 12 is shown. In this embodiment, the ends of optical elements 20 and 30 terminate and flush with the conial face of the tip 12. In this embodiment, the ends are illustrated as having a fiber axis that is parallel to the longitudinal axis of appliance 10.

Figure 3H:
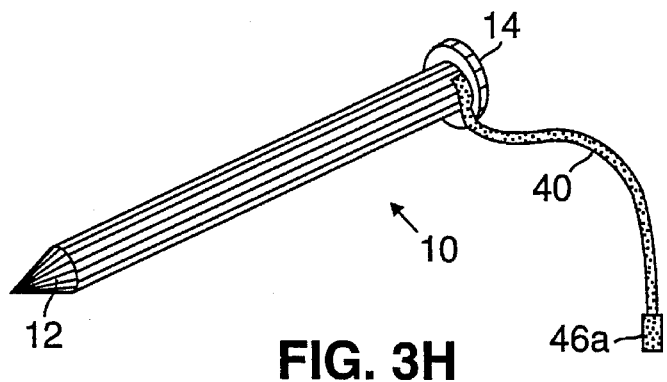
FIG. 3H is an elevated perspective view of a trocar cylindrical tip penetrating appliance in accordance with an embodiment of the present invention.
Figure 3I:
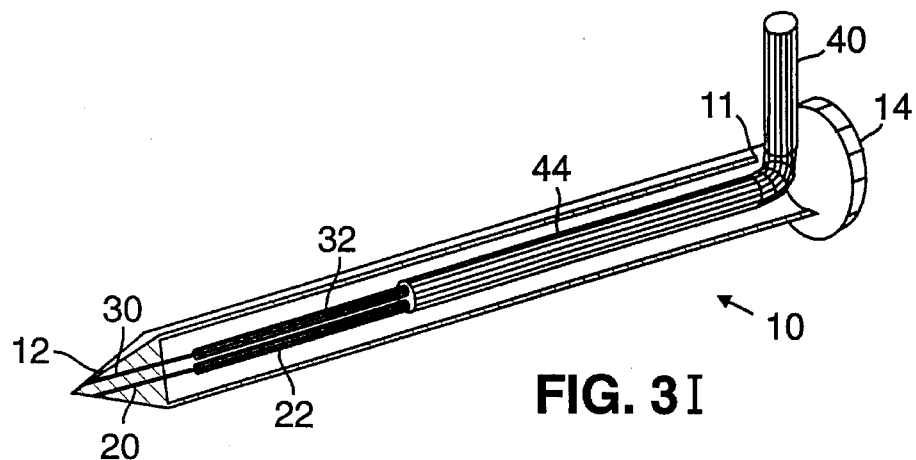
FIG. 3I is a cross sectional view taken along line 3I—3I of FIG. 3H.
Figure 3J:
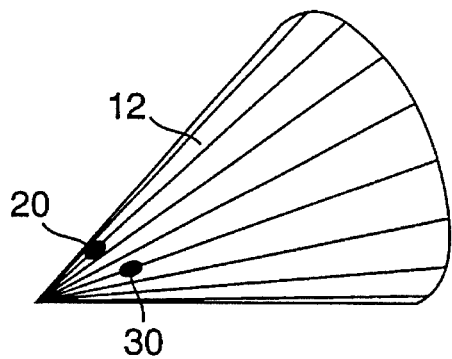
FIG. 3J is a perspective view of the tip of the device of FIG. 3H.
Figure 3K:
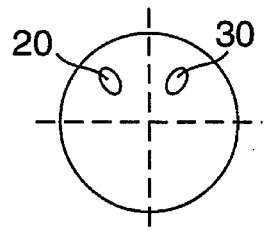
FIG. 3K is an end view of the tip of FIG. 3I.

Referring to FIGS. 3H and 3I, optical elements 20 and 30 are illustrated as the bared ends of a twin (duplex) fiber optical cable 40, wherein optical fibers 20 and 30 are respectively surrounded by separate jackets 22 and 32, and the jackets 22 and 32 are surrounded by a protective cladding 44. In this embodiment, fibers 20 and 30 are bared for a length of 3.175 cm (1.25 inches) and jackets 22 and 32 are exposed for a convenient distance, e.g., between 2 and 10 cm. The protected cable 40 is passed out a port 11 in appliance 10 and terminates in an optical coupler 46a.

As illustrated in FIG. 3I, the ends of fibers 20 and 30 are equispaced on a diameter of the cross section of tip 12 in a plane perpendicular to the axis of tip 12. As noted above, other configurations and positions could be used.

Figure 3L:
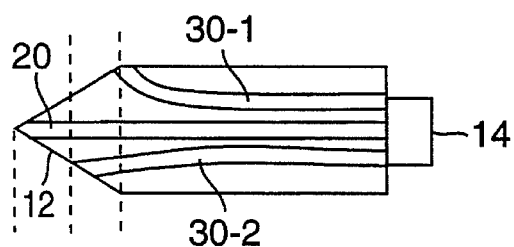

Referring to FIG. 3L, yet another configuration of a trocar tip 12 could include a single optical fiber 20 passing along the axis of tip 12 and terminating with its end in the leading point of tip 12 (or proximate thereto), and using two light detecting fibers 30-1 and 30-2 to detect light illumination in response to the light emitted by fiber 20. Fibers 30-1 and 30-2 are shown as terminating at different distances from the point of tip 12 and on opposite sides of the axis of tip 12, thereby to provide different sensed light signals as described above. Thus, for a pyramid tipped trocar, the ends may terminate in different faces. Alternately, the ends may terminate on the same side of tip 12, e.g., in the same face of a pyramid tipped trocar tip. As used herein, unless otherwise specified, references to the optical elements being "at" the tissue contacting surface should be understood to refer to the end(s) of the optical fiber or the emitting surface of a light source being one of flush with the plane of the tissue contacting surface, a short distance below the plane, or a short distance above the plane, such that the end does not interfere with the mechanical function of the tissue contacting surface.

Referring to FIGS. 4A–4E, the surgical appliance 10 illustrated is a needle having an elliptical tip 12. The ellipsoid is formed in a flat plane at a conventional angle Γ, for example, 15° relative to the longitudinal axis of needle 10. The optical elements 20 and 30 are secured along the minor axis of the ellipsoid plane, on a diameter of the needle 10, disposed in parallel to the longitudinal axis. The elements 20 and 30 are secured by being mounted to needle 20 by epoxy, e.g., Bipax brand optical grade epoxy available from Tra-Con, Milford, Mass. The ends of elements 20 and 30 are polished flush with the flat ellipsoid tip 12.

Figure 4A:
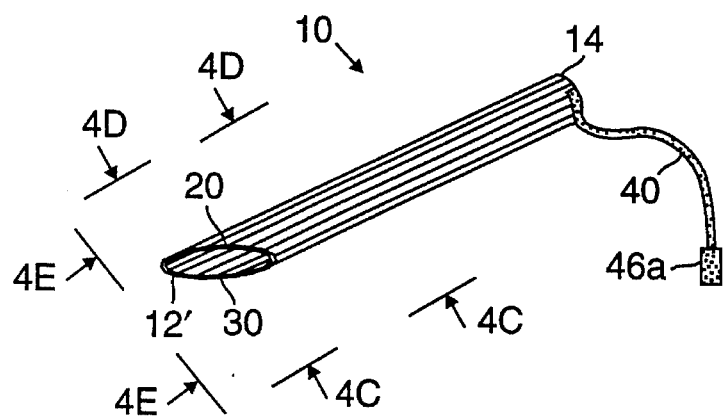
FIG. 4A is an elevated perspective view of an ellipsoid tipped needle type tissue penetrating device in accordance with the present invention.
Figure 4B:
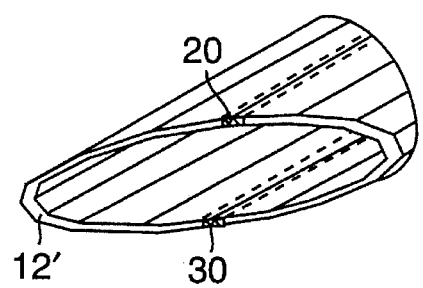
FIG. 4B is an expanded view of the tip of FIG. 4A.
Figure 4C:
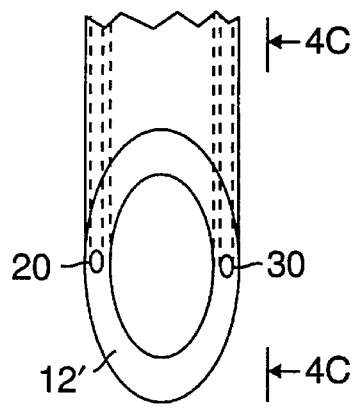
FIG. 4C is a front view taken along line 4C—4C of FIG. 4A.
Figure 4D:
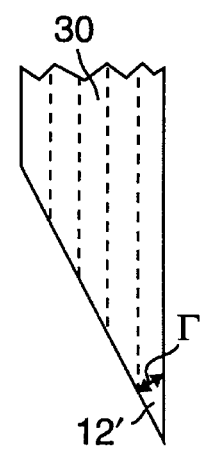
FIG. 4D is a side view taken along line 4D—4D of FIG. 4A.
Figure 4F:
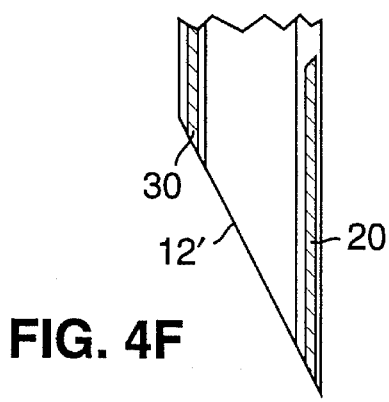
FIG. 4F is a side view of an alternate embodiment of the device tip of FIG. 4A.
Figure 4E:
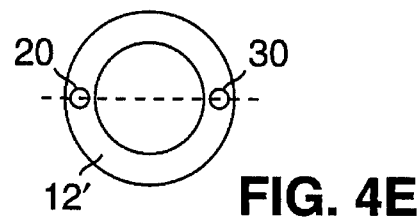
FIG. 4E is an end view taken along line 4E—4E of FIG. 4A.

The ends of optical fibers 20 and 30 are illustrated in FIGS. 4B and 4E as on a diameter of needle 10 and so that they will essentially enter the tissue at about the same time. Alternately, they could be disposed on a chord of appliance needle 10 in a plane perpendicular to the longitudinal axis of appliance needle 10 or in a plane parallel to the tissue contacting face 12'. Further, they may be oriented with one end (preferably the light emitting element) in the lead portion 15 and the other end (preferably the light detecting element) in the trailing portion 15b of face 12' as illustrated in FIG. 4F. This provides for sensing light changes as each of the leading edge 15 and the trailing edge 15b pass into the body cavity.

Alternatively, as noted, elements 20 and 30 may terminate a distance above or below the plane of tip 12 of any appliance 10 providing that such nonplaner termination does not adversely affect the mechanical tissue penetrating function of tip 12. Further, elements 20 and 30 may be secured to needle 10 by being wrapped inside a thin film of material, e.g., mylar. In addition, elements 20 and 30 in the form of optical fibers may be inserted into channels formed in the material of needle 10 (or trocar 10) and sealed in place with an adhesive.

The ends of optical fibers 20 and 30, where they emerge from the surgical appliance 10 to be coplaner with the appliance tissue penetrating tip 12, must be polished. Polishing insures proper mechanical function of the tip and improves the optical coupling of the fibers. The fibers may be polished by the tip sharpening process or they may be polished after tipping by a secondary wet or dry process.

Optical fibers 20 and 30 are preferably routed along the body of appliance 10, preferably inside the body, and more preferably inside passages formed in the material comprising the body. Optical fibers 20 and 30 extend out of the end of appliance 10 through a port in a base 14 (FIGS. 1, 3C, 3D, 4A). Base 14 may interfit with a handle 15. Handle 15 is preferably a durable and reusable body which receives the puncturing tool, e.g. a trocar, and is used to advance the tool into tissue. Handle 15 also may contain a mechanism for controllably advancing the tip 12 relative to handle 15, into the tissue. Handle 15 is illustrated in FIGS. 1B, 1C as a pistol grip, but may have any convenient configuration.

Figure 5:
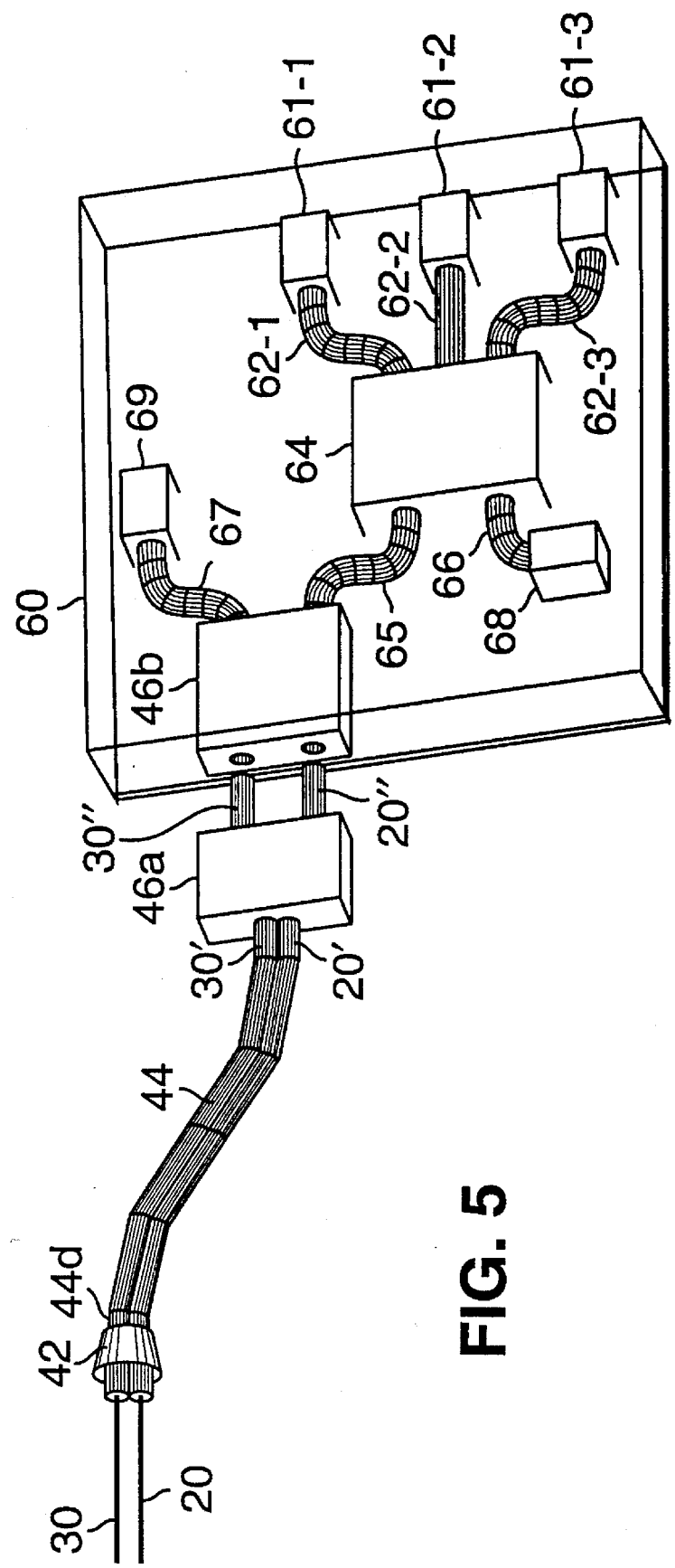
FIG. 5 is a schematic drawing of an embodiment of a synchronous multiplexed optical coupling system for the system of FIG. 1.

Referring to FIGS. 1 and 5, optical fibers 20 and 30 pass through a molded bend relief section 42 and a length of protective cladding 44, and terminate in a conventional plug connector 46a. Plug connector 46a is shown as a male component and has a female counterpart connector 46b which is part of coupler 60. Connector 46a may be a standard duplex connector having two independent optical channels. One channel is illustrated having an input 20' and an output 20" and the other channel is illustrated having an input 30' and an output 30". Female connector 46b is similar. As illustrated in FIG. 1, the length of fibers 20 and 30 may be on the order of 0.5 to ten meters, preferably three meters. Protective cladding 44 and bend relief 42 are conventional structures used to permit repeated flexibility of optical fibers without damaging the fibers. They are not used in the embodiment illustrated in FIG. 1A.

As illustrated in the FIG. 1, 3I, and 4A embodiments, fibers 20 and 30 extend in continuous lengths from tip 12 of instrument 10 to plug connector 46a. Alternately, fibers 20 and 30 may terminate in base 14 of appliance 10 which is in turn connected to fiber cable 40 by conventional optical coupling structures and techniques (not shown). This construction permits using optical fibers between distal end 44a of cabling 44 and connector 46b that are larger dimensioned and more durable optical fiber lengths (See FIG. 1). It also permits using disposable tips 12 (or appliances 10) that are plug compatible with cabling 44 for coupling tip 12 of instrument 10 to coupler 60. Other types of cabling and connectors may be combined to achieve the same function. When a coding system is employed for identifying appliance tips 12 and selecting operating parameters, the code is preferably provided at the junction where the appliance tip 12 is coupled to the control circuits 100. For example, in the embodiment of FIG. 5 the code may be installed in coupler 46a and sensed by a corresponding code reading circuit in coupler 46b, whereas in an embodiment where fibers 20 and 30 terminate in base 14, the code may be provided in base 14 and sensed by a corresponding code reading circuit appropriately.

Additionally, as illustrated in FIG. 1A, it may be possible to eliminate the protective cladding 44 and the corresponding length of optical fibers if coupler 60 and control circuit 100 are made compact and incorporated into the handle 15 of the surgical instrument 10.

Referring to FIG. 5, coupler 60 is an optics module that transmits and receives monochromatic light over optic fibers at n different wavelengths to and from surgical appliance 10, where n is greater than or equal to 2. It has a bulkhead mounted, duplex connector (female) 46b which mates with the male connector 46a at the end of optical cable 44 extending from the surgical appliance 10 (FIG. 1) or with the ends of optical fibers 20 and 30, e.g. at base 14 (FIG. 1A). One optical fiber, or channel, illustrated as channel 65 in FIG. 5, is configured as a transmission channel, and the other channel, illustrated as channel 67 in FIG. 5, is configured as the reception channel. These channels are typically made of the same commercial fiber optic material.

There are at least two methods of combining n different wavelengths and coupling them into an optical fiber, e.g., channel 65, namely synchronous or time multiplexing and wavelength or frequency multiplexing.

Referring to FIGS. 5–9, an optics module 60 using synchronous multiplexing is shown. N different, monochromatic light sources 61-N are provided. Preferably, N=3, which three are illustrated as light sources 61-1, 61-2, and 61-3. Light sources 61-N are preferably light emitting diodes (LEDs), although semiconductor lasers or broadband light sources (e.g., filament bulbs) combined with wavelength selective filters also may be used.

Figure 6:
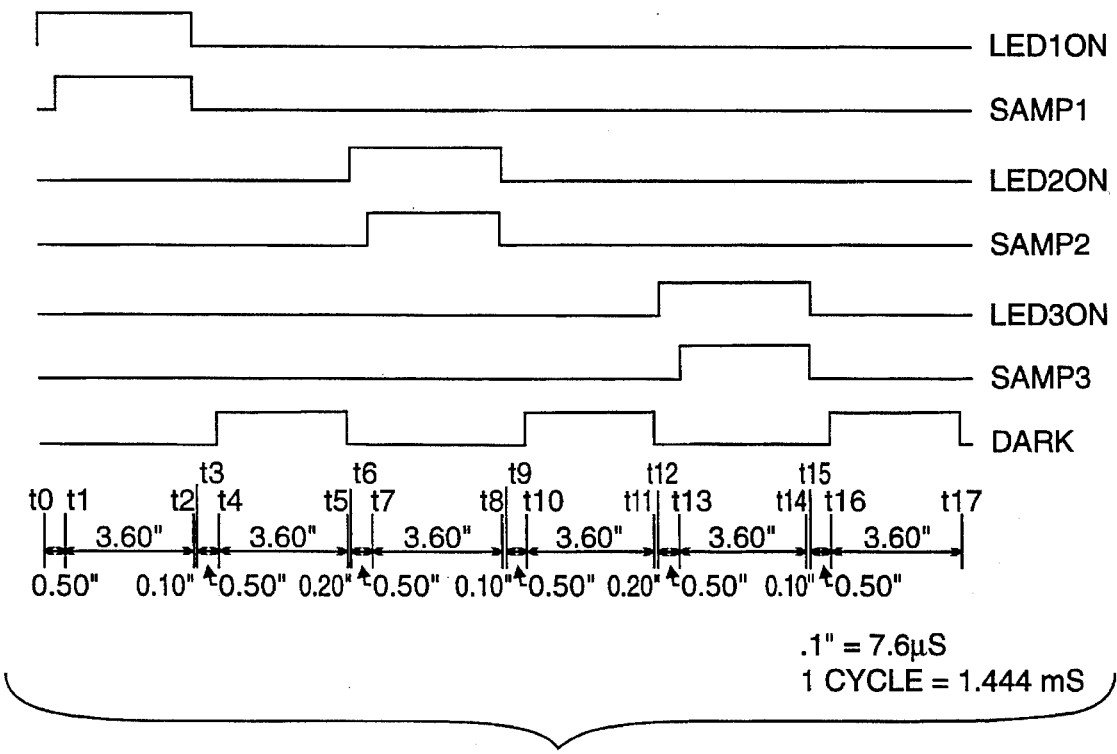
Figure 14:
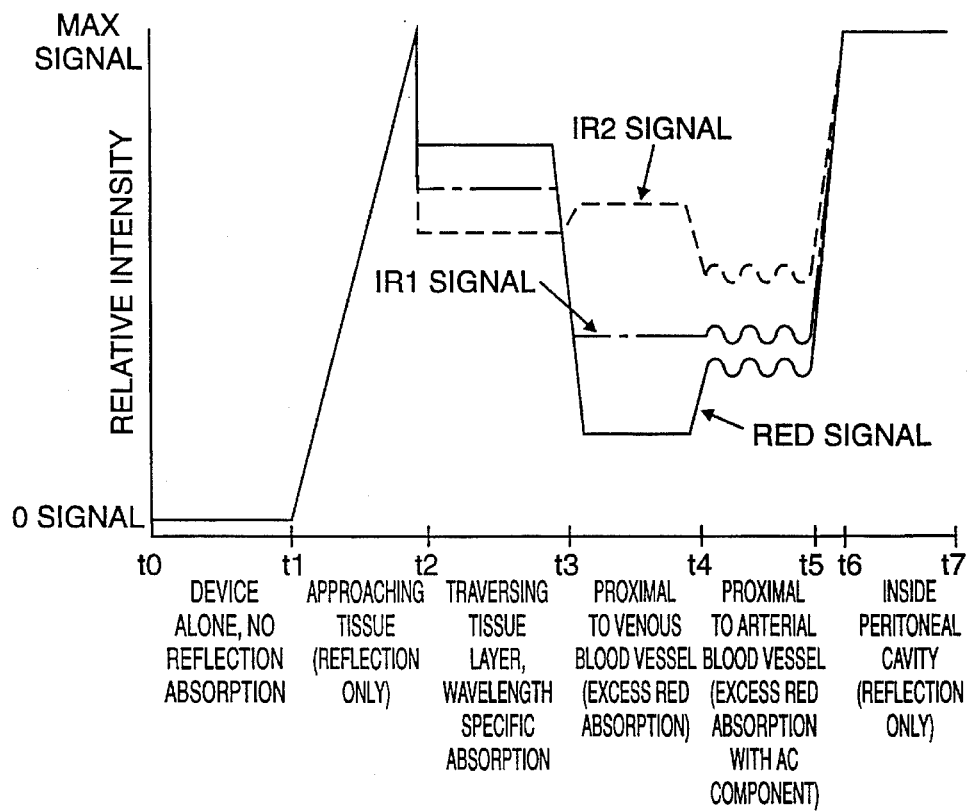
FIG. 14 is a plot of idealized signal waveforms sensed by the light detector of FIG. 8.

The light sources 61-N are energized according to timing control signals. One diagram of suitable timing control signals is illustrated in FIG. 6. The light sources 61-N are respectively connected by fiber pigtails 62-N (i.e., 62-1, 62-2 and 62-3) to an optical coupler 64 such as model #P92-7019-241-1 manufactured by AMP/Kaptron, Harrisburg, Penn. When necessary, optical elements such as lenses may be used to couple light into an optical fiber or to couple light from a fiber to a light detector.

Coupler 64 is a 2×3 coupler which combines the light provided at each of the input fibers 62-N in a symmetric homogeneous fashion and passes it along to each of the two output channels. One output channel is the transmission channel 65 of the front panel connector 46b. The other output fiber optic channel, channel 66, is directed to a photodetector 68, preferably a photodiode such as model #BPX66 manufactured by Siemens Components, Inc., Cupertino, Calif. Detector 68 provides an electrical signal corresponding to the intensity of light emitted by each monochromatic source 61-N. This is used to control the illumination level to avoid intensity drift and to maintain uniform illumination from pulse to pulse of each wavelength.

Reception channel 67 of connector 46b connects the sensed light from surgical appliance 10 and a second light detector 69, preferably a photodiode. Detector 69 provides an electrical signal corresponding to the intensity of light sensed at tip 12 of the surgical appliance 10. This light includes the light reflected by tissue 5 in response to the illumination by sources 61-N. When desired, it may include tissue fluorescence wavelengths.

Referring to FIG. 6, the timing of the operation of light sources 61-N and detector 69 for one cycle is shown. Only one light source 61-N is illuminated at a time according to a selected sequence. After each one light source is illuminated, all of the sources are maintained off for a period of time. Hence, at time t0, the first light source 61-1 is turned on for a pulse duration of about 4.2 time units. At time t1, which is 0.5 time units after light source 61-1 is on, detectors 68 and 69 are turned on to sense light illumination for a pulse duration of 3.6 time units. Detectors 68 and 69 are then turned off at time t2, about 0.1 time units before source 61-1 is turned off at time t3. After source 61-1 has been turned off for 0.5 time units, detectors 68 and 69 are turned on at time t4 and off at time t5, for a pulse duration of 3.6 time units, to sense the dark illumination.

After a delay of 0.2 time units, the next light source 61-2 is turned on at time t6 for a pulse duration of 4.2 time units. Detectors 68 and 69 are turned on to sense light illumination at time t7 for a pulse duration of 3.6 time units in the same manner as described previously in connection with source 61-1. After the second light illumination sample is obtained, detectors 68 and 69 are turned on to sense the dark illumination. Similarly, the third light source 61-3 is illuminated and a third light illumination sample is obtained by detector 69, followed by a dark illumination sample. The cycle then repeats. Detectors 68 and 69 are turned on 0.5 time units after source 61-N is turned on to allow source 61-N to reach a steady state light illumination at a selected intensity level (as adjusted in response to the light illumination intensity sensed by detector 68), and 0.5 time units after source 61-N is turned off to allow the tissue to reach a steady state dark illumination condition. A clock frequency of 514 Hz may be used to operate sources 61-N and detector 69, such that a complete illumination and sampling cycle occurs every 1.444 ms, and a time unit of 1.0 corresponds to 76 microseconds. Other cycle times and time units may be used, including illumination pulses of different durations for the different light sources, and for the detectors light and dark illumination sampling.

Figure 7:
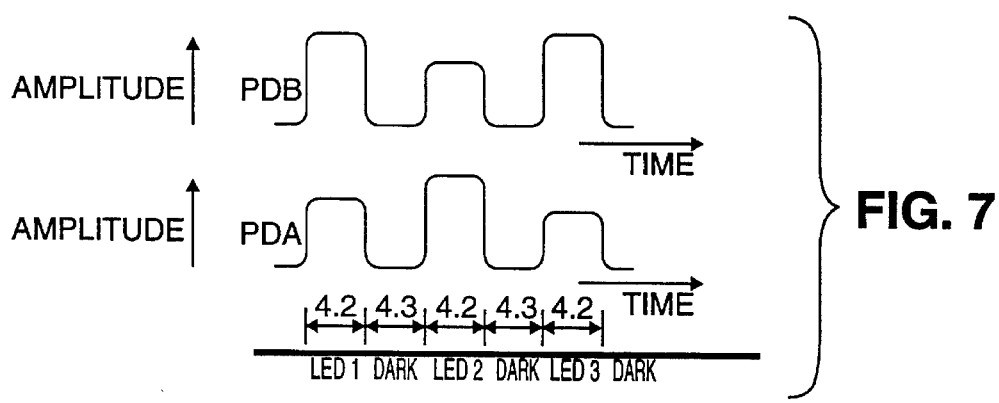
FIG. 7 is a plot of sensed illuminations over time of the light detector of FIG. 5.

Referring to FIG. 7, the intensity signals sensed by detectors 68 and 69 are illustrated as signal PDB and PDA, respectively, in arbitrary amplitude units versus time. The waveforms illustrated have different amplitudes for the different wavelengths, namely LED1, LED2, and LED3, corresponding to the relative sensed light intensity of signal PDA being different from the relative emitted light intensity of signal PDB. Each source 61-N is illuminated for a period of 4.2 time units, one at a time, such that a dark illumination period of 4.3 time units occurs between each one source illumination. These signals are processed by control circuit 100 to extract n signals (n=N) corresponding to the light and dark illumination sensed by detector 69 at the tissue (signal PDA) and n signals corresponding to the light and dark illumination sensed by detector 68 at each source 61-N (signal PDB).

Figure 9:
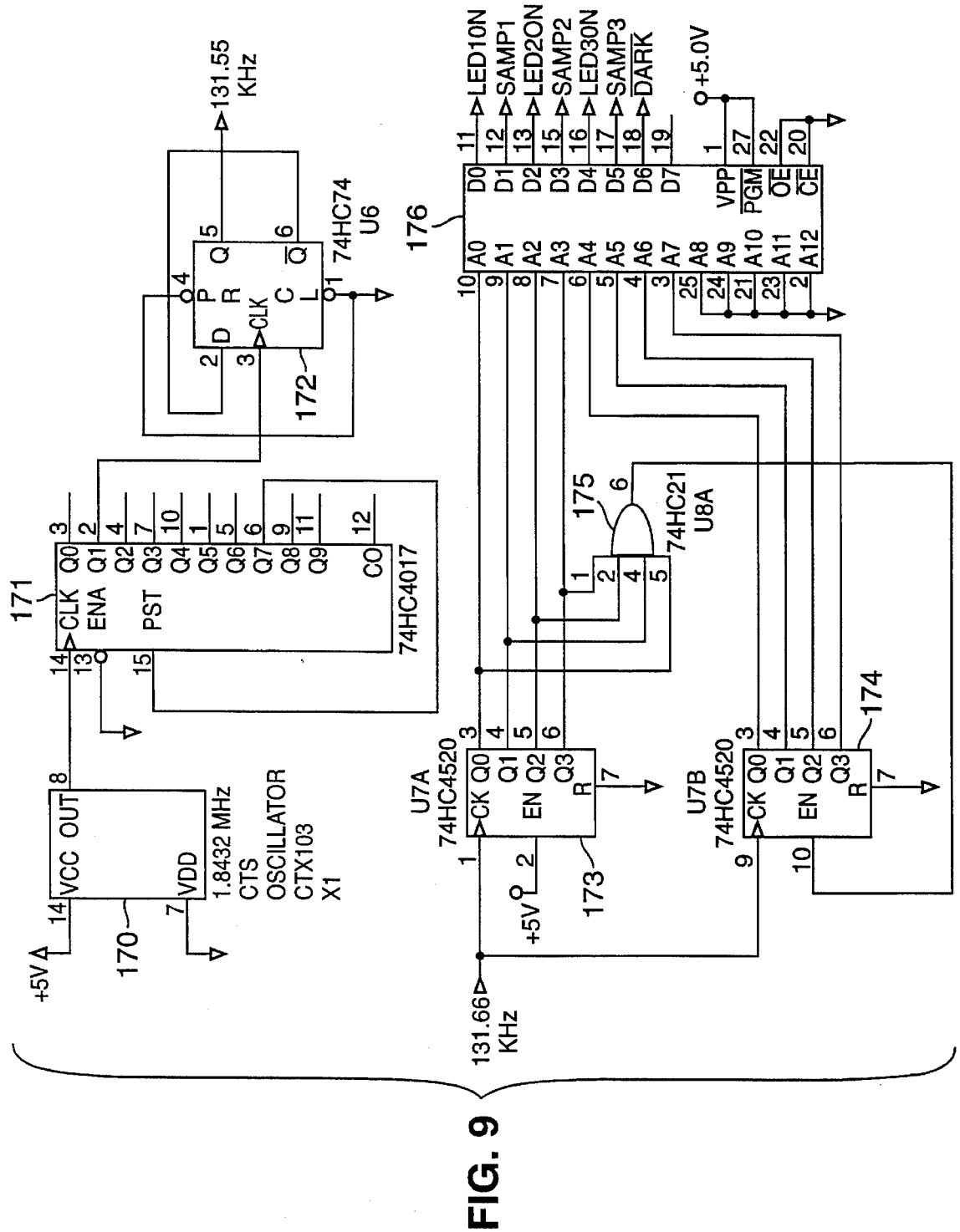
FIG. 9 is a schematic circuit diagram of the control circuit of FIG. 8.

Control circuit 100 is the electronics module illustrated in FIGS. 8 and 9. Circuit 100 may be configured to provide a set of n+1 square waves labeled LED1ON, LED2ON, LED3ON and DARK (shown in FIG. 6A). These signals are used to turn light sources 61-N on or off and, as explained below, to gate the electrical signals generated by light detectors 68 and 69 into different output channels.

Timing signal DARK provides a first pulse which designates a light source off or dark illumination period in the detector signal. This is used to provide a reference dark illumination signal for each discrete wavelength that can be used to subtract out the detector offset or ambient light contributions, for each of photodetectors 68 and 69. The pulse width or operating frequency of the timing waveform is chosen to be fast enough to minimize the 1/f noise characteristic of the photodetector and slow enough to keep the cost of the electronics low. A pulse width of 50 to 100 microseconds is suitable. The operating frequency also is chosen to avoid common line frequencies and their harmonics, thereby to avoid aliasing effects from electronic interference or fluctuating ambient light levels.

The timing diagram of FIG. 6 utilizes 2*n square wave signals where n off states are provided immediately following each of the n light source on states. This system more thoroughly eliminates time varying detector offsets (i.e., drift) and ambient light contributions. However, this system has a longer pulse string and will have a longer response time for a given pulse width (operating frequency).

Figure 10:
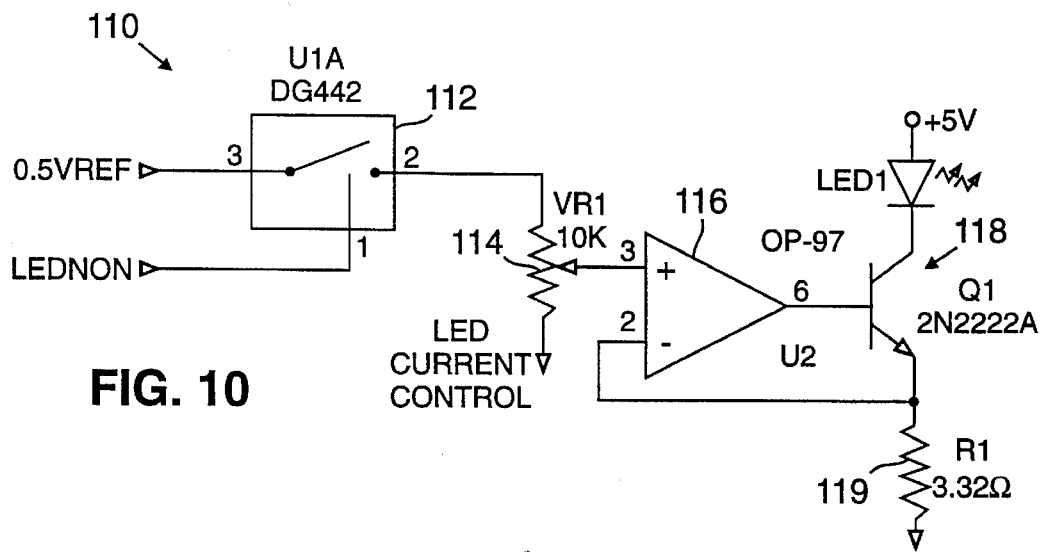
FIG. 10 is a schematic circuit diagram of the analog circuit for driving a light source of FIG. 8.

Referring to FIGS. 8 and 10, each light source 61-N is a light emitting diode (LED) and has a drive circuit 110-N (reference 110 in FIG. 11) which is a constant current source. Drive circuit 110 has a switch 112, a potentiometer 114, an operational amplifier 116, a bipolar transistor 118, and a resistor 119 configured as shown. Switch 112 is preferably an analog switch, model DG442, available from Siliconix, Santa Clara, Calif. It has two inputs, one labeled 0.5REF which is a reference voltage of 0.5 volts, and one labeled LEDNON (the first N=1, 2, 3). Potentiometer 114 is a 10 Kohm potentiometer that is used to provide a control voltage of between 0 and 0.5 volts to the base of transistor 118. Amplifier 116, preferably a PMI Model No. OP-97 analog low noise low offset amplifier, and transistor 118, preferably a type 2N2222A transistor, are operated in a closed loop so that the voltage from the wiper of potentiometer 114 appears across a 3.32 ohm current monitoring resistor 119 in the emitter of transistor 118. Transistor 118 thus serves as a current amplifier. LED 61-N is located in the collector of transistor 118 with its anode connected to a +5 volt source. When the signal LEDNON is low, switch 112 is open, the control voltage is zero and no current will flow through LED 61-N, which is not illuminated. When signal LEDNON is high, switch 112 is closed, the control voltage 0.5REF is connected to the non-inverting input of amplifier 116 across potentiometer 114 which turns on LED 61-N. For a control voltage of 0.5 volts and using a 3.32 ohm current monitoring resistor there will be about 151 mA of current through LED 61-N. LED 61-N turns off when signal LEDNON is again brought low.

Potentiometer 114 provides for adjusting the brightness of LED 61-N manually. It may be replaced by a fixed resistor. More preferably, the brightness may be controlled by suitable hardware or microprocessor controlled software, e.g., under servo loop control, to maintain the received signal optimized within a selected range appropriate for the given circumstances. In a preferred embodiment, the brightness of each LED 61-N may be independently controlled by circuit 110-N, manually by potentiometer 114-N or under software control, so that the signal strength of each wavelength can be optimized. Alternately, all of the light sources 61-N could be operated from a single, common variable adjustment, e.g., one potentiometer (not shown) for brightness control.

Figure 11:
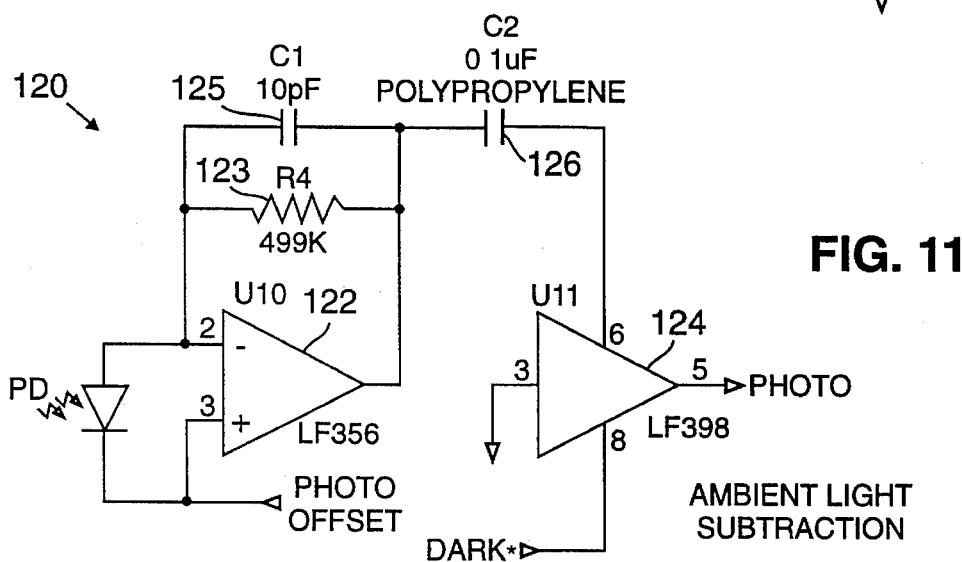
FIG. 11 is a schematic circuit diagram of the analog circuit for operating a light detector of FIG. 8.

Referring to FIGS. 8 and 11, preamplifier circuits 120A and 120B are respectively provided for light detectors 69 and 68. Preamplifiers 120A and 120B are used to condition and amplify each electrical signal generated in response to the sensed light and dark illuminations. Each circuit has a gain of about 0.499 V/μA. Circuits 120A and 120B each include a photodiode PD (i.e., detector 69 or 68) and an operational amplifier 122 (type LF356) configured with a 499 Kohm resistor 123 and a 10 pF capacitor 125 in the inverting feedback loop. Capacitor 125 provides a single pole filter at about 32 KHz. Photodiode PD is connected between the inputs of amplifier 122. The non-inverting input of amplifier 122 receives the signal PHOTO OFFSET, a +10 volt reference signal, which is used to increase the dynamic range of amplifier 122 by a factor of 2 to plus and minus 10 volts.

The output of amplifier 122 is coupled to pin 6 of a sample and hold amplifier 124 (type LF398) across a 0.1 microfarad capacitor 126. During the dark time, pin 6 is essentially switched to ground. Capacitor 126 then acquires the ambient light value. During the time that the LED 60-N in on, capacitor 126 subtracts the dark illumination from the sensed light illumination, and amplifier 124 provides the amplified ambient light compensated output signal PHOTO. The preamplifier 120 may incorporate adjustable gain stages, preferably controlled by a software servo.

Referring to FIGS. 8 and 13, the signals PHOTO (PHOTOA from detector 69 and PHOTOB from detector 68) are respectively passed to separate demultiplexer (demodulator) circuits 130. The demultiplexed signals are in turn each passed to a low pass filter 140. Each demultiplexer circuit 130 comprises a series of switches and is used to gate the correct portions of the photodetector signal PHOTO, corresponding to a selected wavelength, into the correct output channel for that wavelength. The switches also function to invert the dark state of the photodetector signal and sum it into all of the output channels. The low pass filters 140 are provided to smooth out the carrier (switching) frequency without compromising the physiological signals.

The 2n output channels (n tissue measurements and n reference measurements) are preferably configured as voltage inputs to an analog to digital converter (not shown). The output of the analog to digital converter is then provided to a signal processing circuit or device (not shown), e.g., a microprocessor controlled device such as a personal computer, for further analysis and computation under software control. Alternately, the 2 n channels are passed to analog and/or digital circuits for comparing the demultiplexed sensed light illumination signals for the selected wavelengths to one or more thresholds and making determinations based on those comparisons. In this embodiment, the thresholds may be selected to indicate relative progress of tip 12 through the tissue into a body cavity. It is to be understood that demultiplexing and filtering of the sensed analog light and dark illumination signals can be achieved by any of a number of techniques.

In the embodiment illustrated in FIG. 8, there are two demultiplexers 130A and 130B, one for each of photodetectors 68 and 69. In this regard, amplifier 120A produces output signal PHOTOA corresponding to the light intensity sensed at tip 12. Amplifier 120B produces output signal PHOTOB corresponding to the illumination intensity at each source 61-N. Each signal PHOTOA and PHOTOB is multiplexed and contains the three discrete light illumination samples in response to the wavelengths emitted by sources 61-N, N=1, 2, and 3, and the intervening dark illumination samples (see FIGS. 6 and 7).

For convenience of construction, each multiplexed photodetector output PHOTOA and PHOTOB is passed to three separate signal processing circuit channels 125, one of which is illustrated in FIG. 13. Each channel 125 has the same demultiplexing circuit 130 and low pass filter 140. Each demultiplexer circuit 130 responds to one timing control signal SAMPN (where N=1, 2 or 3) and one output signal PHOTOX (where X=A or B) and its associated low pass filter 140 provides a demultiplexed output signal "SIGNAL X, N". Thus, the six processing circuit channels 125 yield the six signals shown in FIG. 8, namely SIGNAL A,1, SIGNAL A,2, SIGNAL A,3, SIGNAL B,1, SIGNAL B,2, and SIGNAL B,3.

Referring to FIG. 13, demultiplexer 130 of each channel 125 includes switch 132 for gating in the one photodetector signal PHOTOX only in response to the one control signal SAMPN. Switch 132 is on for 36/256 of a cycle according to the control circuit of FIG. 9 described below. The gated-in signal is low-pass filtered across an 11 Kohm resistor 133 and a 0.1 microfarad capacitor 134, into the noninverting input of an operational amplifier 135. The filtering is at about 20 Hz. Amplifier 135 is configured as a unity gain buffer amplifier. The output of amplifier 135 is passed to low pass filter 140.

Low pass filter 140 is constructed as a four pole, 10 Hz, low pass filter having two Sallen-Key component value two pole filters with a dumping factor of about 1.4 to provide a classical Butterworth type response, as illustrated. Each two-pole filter includes a pair of low pass filters comprised of 158 Kohm resistor 141 and a 0.1 microfarad capacitor 142, and the filtered signal input to the non-inverting input of an operational amplifiers 143. Amplifier 143 has a feedback voltage divider at the inverting input using a 169 Kohm resistor 144 and a 100 Kohm resistor 145. The output of the first stage is input to the input of the second stage, and the output of the second stage is one of the six demultiplexed signals SIGNAL X,N.

Figure 18A:
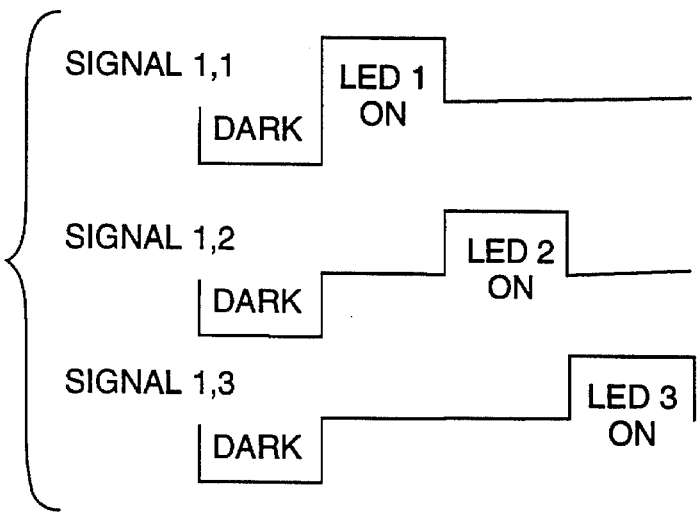
FIG. 18A shows representative output signals corresponding to three selected wavelengths of the timing diagram of FIG. 6A.
Figure 18B:
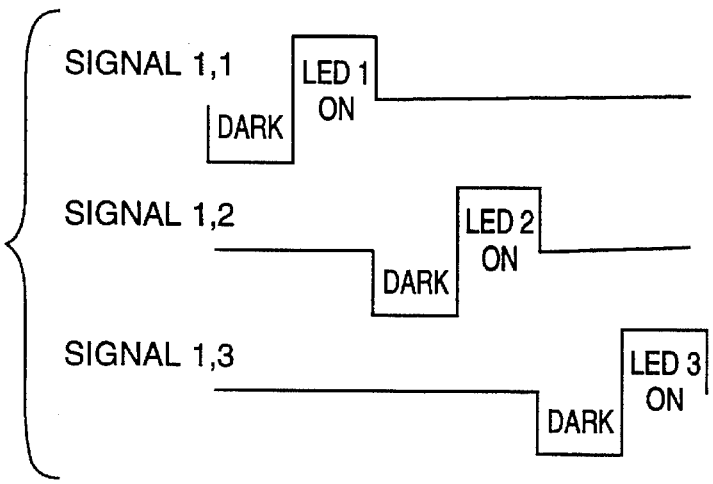
FIG. 18B shows representative output signals corresponding to three selected wavelengths of the timing diagrams of FIG. 6.
Figure 18C:
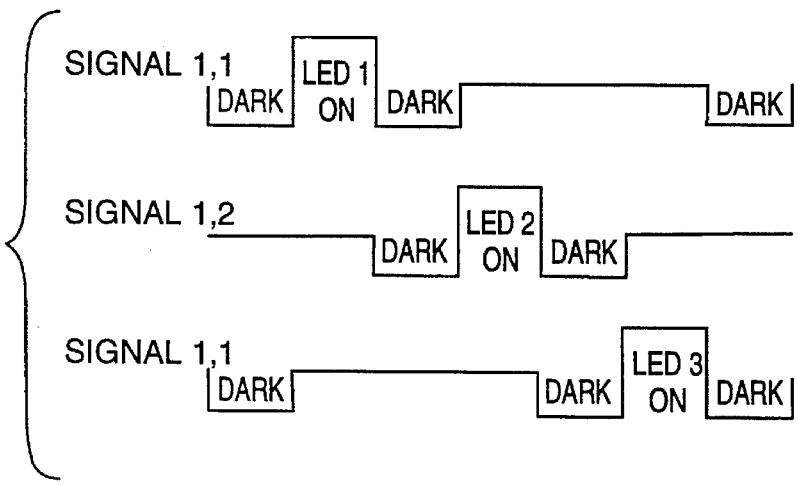
FIG. 18C shows representative output signals corresponding to selected wavelengths for a timing diagram of an alternate embodiment of the invention.

FIGS. 18A–18C illustrate three different possible waveforms for the demultiplexed signals SIGNALX,1, SIGNALX,2 and SIGNALX,3, for X=A or B. FIG. 18A corresponds to the timing pulses of FIG. 6A, where there is one DARK signal pulse for each wavelength illumination cycle. FIG. 18B corresponds to the timing in FIG. 6 where there is a dark illumination sample obtained before each light source 61-N is illuminated. FIG. 18C corresponds to a timing diagram having 2n+1 signals which can be implemented by the design of FIG. 6 using one additional timing state to obtain a dark illumination sample before and after each light source 61-N is illuminated.

Figure 12:
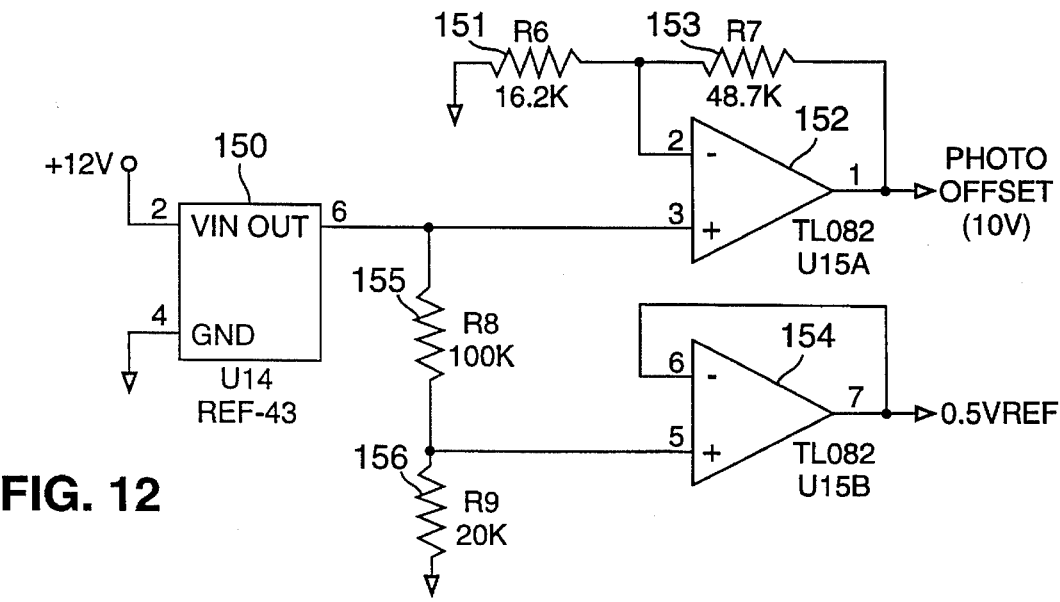
FIG. 12 is a schematic circuit diagram of the analog circuit for producing regulated voltage supplies for the current of FIG. 8.

Referring to FIG. 12, a regulated power supply 150, operating off a +12 volt supply (e.g., a rechargeable battery or a transformer from line current), is shown. Amplifier 152 is configured with resistors 151 and 153 for providing the reference signal PHOTO OFFSET at +10 volts. Amplifier 154 is configured with resistors 155 and 156 to provide the signal 0.5 VREF at 0.5 volts, by appropriate amplification and voltage division from the output of regulator 150. These reference signals also may obtained in any other conventional manner.

Figure 6A:
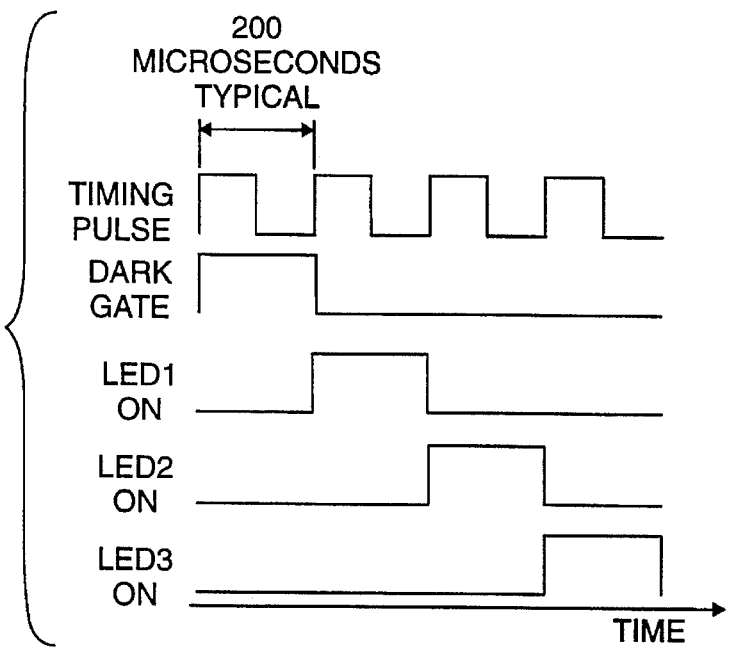
FIG. 6A is an alternate timing diagram for operating the light sources of FIG. 5.

Referring to FIG. 9, the circuit elements of control circuit 100 for providing the timing signals illustrated on FIGS. 6A and 18A are shown. These elements include a crystal oscillator clock 170, a plurality of flip flops 171–174 and a memory device 176 which is used as a configurable switch. Clock 170 is a 1.8432 MHz oscillator (model CTX103, e.g., Model 50F1209, available from Newark). The clock signals are divided down by seven across a flip flop 171 (a model 74HC4017, available from Motorola) and by two across a flip flop 172 (model 74HC74, available from Motorola) to provide a clock frequency of 131.66 KHz. That clock signal is simultaneously input into two flip flops 173 and 174 (model 74HC4520, available from Signetics) which are used to divide synchronously the 131.66 KHz clock by 2, 4, 8, . . . and 256, each of flip flops 173 and 174 has four state outputs. A +5 volt reference is input into flip flop 173 and the four output channels of flip flop 173 are passed to the input of an OR gate 175 (e.g., model 74HC21, available from Texas Instruments). The output of OR gate 175 is fed back to the reference input of flip flop 174. As a result, the output of flip flop 174 provides the inverse of the timing signals of flip flop 173. All eight flip flop outputs are used to drive the address inputs of a memory device 176 (model 27C64, available from Texas Instruments). Device 176 is preferably an erasable programmable read-only memory (EPROM), that is programmed with the desired timing, and control signals, e.g., LED1ON, LED2ON, LED3ON, SAMP1, SAMP2, SAMP3, and DARK as illustrated on FIG. 6 or 6A. In a preferred embodiment, the pattern programmed in EPROM 176 is selected to repeat in a cycle of 514.3 Hz. This frequency was chosen so that interference from 60 Hz sources could be filtered without losing the desired biological signals. The outputs of EPROM 176 drive the other circuitry of circuit 100.

Referring again to FIGS. 2A–2H and 14, a plot of idealized, representative waveforms of light sensed by photodetector 69 over time, under varying conditions, are shown. Three waveforms are provided for three sources 61-N, such that source 61-3 is an infrared light wavelength at 940 nm, source 61-2 is an infrared light wavelength at 810 nm, and source 61-1 is a red light wavelength at 660 nm. Other wavelengths and more or fewer wavelengths also could be used. LEDs are preferred because they have low cost, long life, and are relatively monochromatic. The plot from time t0 to t1 represents the dark illumination, when none of the light sources is emitting, and there is no absorption or reflection of light from tissue 5. The time period from t1 to t2 illustrates light illumination corresponding to the increase in reflection as tip 12 containing optical elements 20 and 30 is gradually brought closer to the tissues. See FIG. 2A.

The time period from t2 to t3 represents differences in wavelength specific light absorption when tip 12 is stationary in contact with tissue 5 (FIG. 2B). In this case, the two infrared and one red light wavelengths are absorbed by the tissue at different intensities. The light illumination sensed by photodetector 69 at each of the wavelengths differs according to the different relative absorptions. As tip 12 progresses toward the distal side of tissue 5, the amplitude of the absorbed light component will change, corresponding to changes in tissue thickness and the relative reflection and absorption of each wavelength.

The time period from t3 to t4 represents differences in wavelength specific light absorption when tip 12 is stationary in contact with venous blood vessels. In this case, there is relatively greater red light absorption. This is reflected in the proportionately lower amplitude of light illumination sensed for the red versus infrared wavelengths. See FIG. 2B.

The time period from time t4 to time t5 represents the differences in wavelength specific light absorption when tip 12 is stationary in contact with arterial blood vessels. In this case, there is relatively greater red light absorption, and all of the red and infrared light illumination wavelengths are modulated by an alternating component corresponding to pulsatile arterial blood flow. See FIG. 2B. In these cases, as tip 12 progresses through tissue 5, the sensed light illumination amplitude of the absorbed light component will change, corresponding to changes in tissue thickness and the alternating component will change as less pulsatile tissue is illuminated.

The time period from time t5 to t6 represents the decrease in absorption as the tip 12 passes through the distal side of tissue 5 and into the peritoneal cavity (at time t6). Inside the cavity, e.g., from time t6 to t7, the sensed light illumination is primarily the reflection component, as there is minimal light absorption in the cavity. This produces a relative maximum signal on photodetector 69.

Control circuit 100 thus may provide for generating audible alarm signals corresponding to the sensed light illumination indicative of tip 12 passing through and, more particularly, into the tissue. The alarm signal may be broadcast on annunciator 70 as previously described. It should be understood that different placements and orientations of the ends of elements 20 and 30 relative to each other and relative to the tissue contacting surface(s) of tip 12 of appliance 10 will produce different characteristic light illumination signals. Thus, the placement and orientation of elements 20 and 30 is a matter of design choice and control circuit 100 is to be adapted to sense and discriminate the particular characteristic light illuminating signals and relative changes in those signals as appliance 10 moves in penetrating contact with the tissue.

Figure 17:
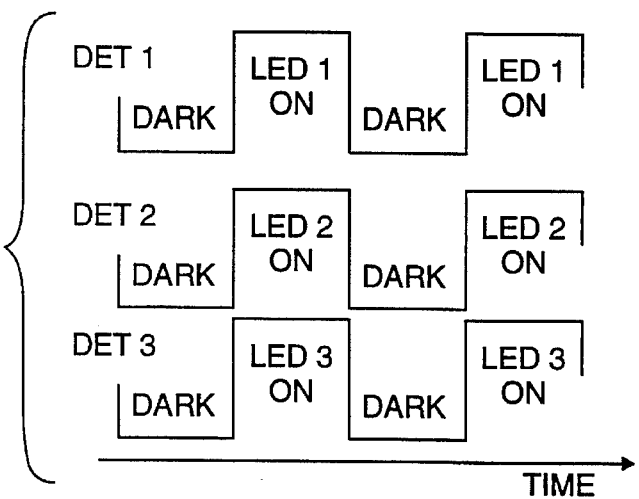
FIG. 17 is a timing diagram of the signals on the righthand side of FIG. 16 before the low pass filter.
Figure 15:
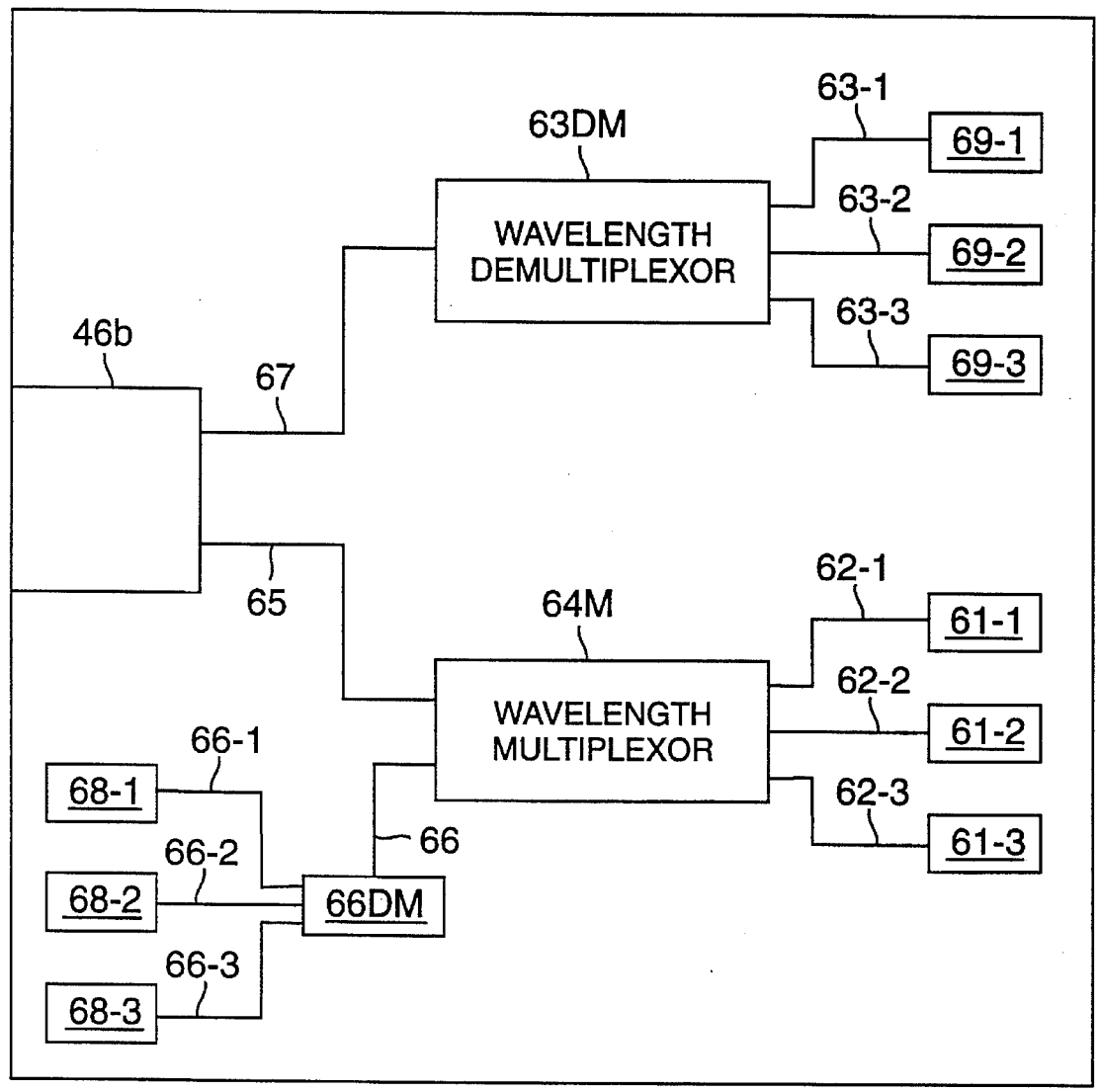
FIG. 15 is a schematic drawing of an embodiment of a wavelength multiplexed optical coupler for the system of FIG. 1.
Figure 16:
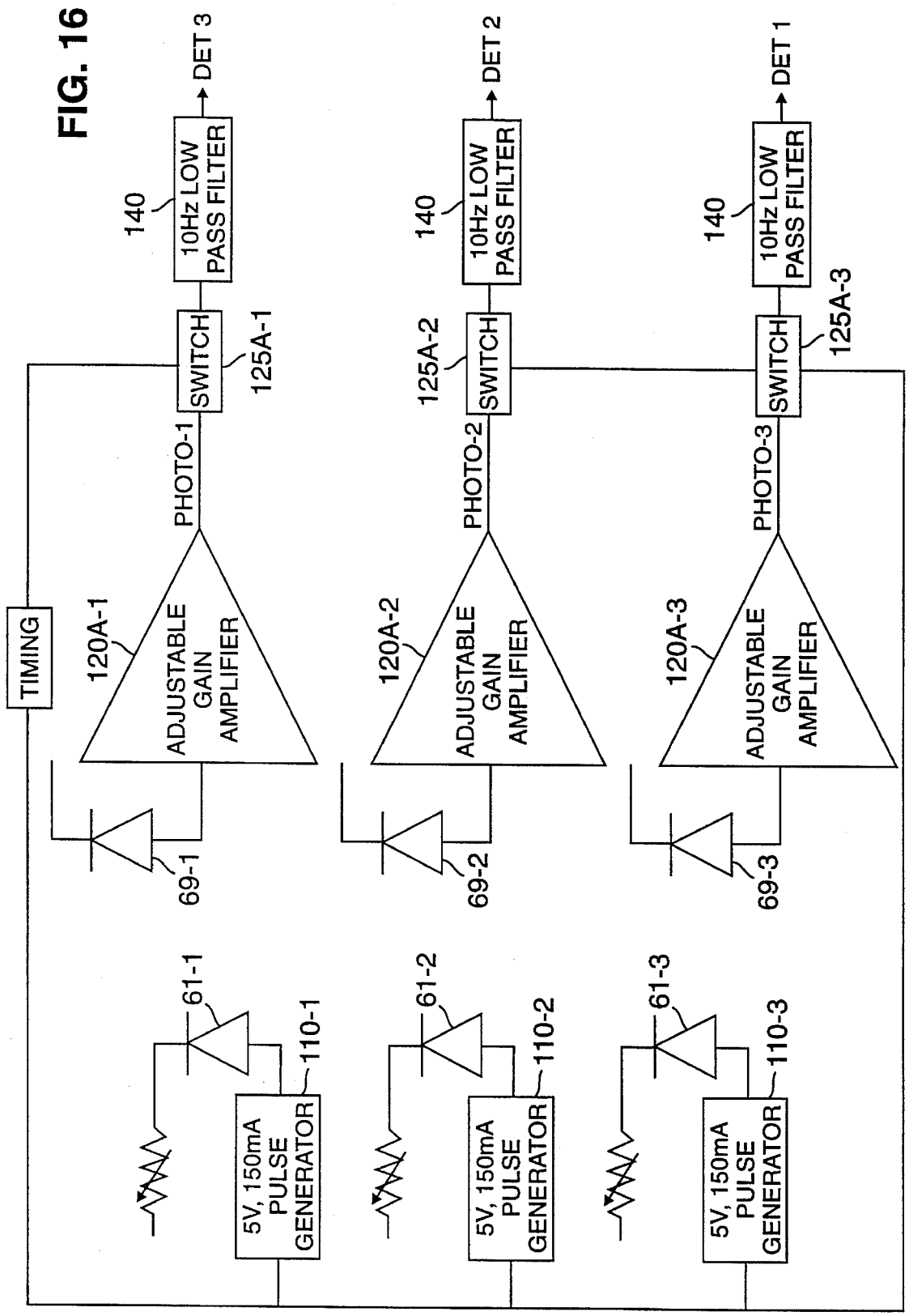
FIG. 16 is a schematic circuit diagram of the control circuit of the system of FIG. 15.

Referring to FIGS. 15–17, a wavelength multiplexing scheme is shown. In this design, separate photodetectors 69-N and 68-N are provided for each of the n wavelengths emitted by sources 61-N. The light from each of sources 61-N is launched into fiber pigtails 62-N, which combine in a wavelength multiplexing coupler 64M, such as models #99100-3 or 99103-3 available from AMP, Inc., Harrisburg, Penn. The output fiber of coupler 64M is routed to the transmission channel 65 of the bulkhead connector 46b. Coupler 64M has the same characteristic of combining light in a symmetric, homogeneous fashion as 2×3 coupler 64 illustrated in FIG. 5.

The reception channel 67 of the bulkhead connector 46b is directed to a wavelength demultiplexing coupler 63DM, such as models #99100-3 or 99103-3 available from AMP, Inc. Each output pigtail 63-N of demultiplexer 63DM, which contains one wavelength signal N is routed to an individual light detector 69-N (photodiodes are preferred). Similarly, a second output of coupler 64M is passed to a second wavelength demultiplexing coupler 66DM and then by pigtails 66-N to detectors 68-N. This scheme provides n discrete detectors 68-N to monitor sensed light and dark illumination at sources 61-N and n discrete detectors 69-N to monitor sensed light and dark illumination at tissue 5 at tip 12 of surgical appliance 10. No additional electronic signal multiplexing or conditioning is required.

In this wavelength multiplexing embodiment, the timing function is much simpler because each light source may be illuminated simultaneously. Hence, a single square wave denoting on and off states is adequate. The dark illumination may be sampled during each off state, following the aforementioned delay. The same frequency of illumination and sampling described above may be used, except that all of the light sources are on and off simultaneously.

The light source drive circuit 110 and photodetector preamplifier 120 may be the same as those described in connection with the synchronous multiplexer system, except that the photodetector preamplifier 120 must be repeated for each of the photodetectors 68-N and 69-N. Thus, each amplifier 120X-N provides an output signal PHOTO X-N, for X=A or B and N=1, 2 or 3.

The PHOTO X-N signals are separately processed. FIG. 16 illustrates detectors 69-N and the corresponding amplifiers 120A-N, switches 125A-N and low pass filters 140. Switch 125A-N is a network that inverts and sums the off state signal. An identical low pass filter 140 is provided for each separate signal PHOTO X-N to smooth out carrier frequencies. The output of filters 140 for PHOTOA-N is illustrated as signals DET-N, for N=1, 2 or 3 on FIG. 17. The 2n output channels (n tissue measurements and n reference measurements) are further processed, e.g., configured as voltage inputs to an A/D convertor and digitized for further analysis and computation in a computer, or passed to an analog/digital threshold comparator network, in the same manner as previously described. The synchronous multiplexing technique uses fewer optical and detector components than the wavelength, but it requires additional electronic switching and processing.

It should be understood that other than microprocessor based devices could be used to indicate when appliance tip 12 has penetrated into a body cavity. Desirably, simple and less expensive analog circuits using various signal comparators having selected, adjustable reference thresholds and sample and hold circuits could be used to detect desired substantial changes in light illumination sensed at the tissue, corresponding to passage of the tip 12 therethrough. Also, solid state finite machines could be used to implement the signal processing of the present invention. In either embodiment, setting the desired threshold levels are selected as a matter of design choice and may be encoded or calibrated for each patient, e.g., using the light illumination sensed at the position illustrated in FIG. 2A to set the thresholds for the alarm signals on annunciator 70.

Appropriate selection of the intensity of emitted light from sources 61-N and threshold values for processing the sensed light illumination samples may make it unnecessary to subtract out the dark illumination intensities to identify tip penetration. In this case, the dark illumination level can be not used or sensed, or more preferably, sensed and used to indicate when the ambient light conditions may lead to inaccurate sensed light illumination determination. Thus, the operator can adjust the ambient light conditions accordingly. If the dark illumination is not required, the light source 61-N may be operated continuously and detectors 68 and 69 may operate continuously or be strobed periodically to obtain light illumination samples.

One skilled in the art will appreciate that the present invention can be practiced by other than the described embodiments which are presented for purposes of illustration and not of limitation.

We claim:

1. A tissue penetrating appliance comprising:
   a sharp tip having a tissue contacting surface configured to penetrate tissue and a longitudinal axis, the tissue contacting surface having a first face lying in a first plane at an angle relative to the longitudinal axis;
   a first light transmitting optical element connected to the tip having a first end to emit one or more selected wavelengths of light from a first location on the tissue contacting surface and having a second end; and
   a second light transmitting optical element connected to the tip having a first end to receive light corresponding to the one or more selected wavelengths of light at a second location on the tissue contacting surface and having a second end,
   wherein the first and second optical elements are secured to the appliance, the first and second locations are spaced apart, the first optical element first end terminates in the first face in the first plane, and the second optical element first end terminates in the tissue contacting surface;
   a first fixture receiving the second ends of the first and second optical elements;
   a source of light having one or more monochromatic wavelengths;
   a light detector responsive to a sensed light intensity having an electrical signal corresponding to the sensed light intensity;
   a first coupler having a transmission channel input and output and a reception channel input and output, the transmission channel comprising an optical fiber connected to transmit light emitted by the light source to the transmission channel output, the reception channel comprising an optical fiber connected to transmit light coupled to the reception channel input to the light detector, the first coupler being coupled to the first fixture so that the reception channel input is in optical communication with one of the first and second optical elements and the transmission channel output is in optical communication with the other of the first and second optical elements;
   a control circuit connected to the light source having a first state to cause the light source to emit light at the one or more wavelengths and said light received at the first end of the other of the first and second optical elements is coupled to the light detector to provide an electrical signal corresponding to said received light; and
   means for processing the provided electrical signals and determining when the appliance tip has entered a body cavity.

2. The apparatus of claim 1 further comprising an annunciator wherein the processing means actuates the annunciator when the tip has entered a body cavity.

3. The apparatus of claim 2 wherein the processing means further actuates the annunciator to produce a variable signal corresponding to the extent that the tip has passed into the tissue.

4. The apparatus of claim 1 wherein each of the first and second optical elements further comprises a length of fiber optic conductor.

5. A tissue penetrating appliance comprising:
   a sharp tip having a tissue contacting surface configured to penetrate tissue and a longitudinal axis, the tissue contacting surface having a first face lying in a first plane at an angle relative to the longitudinal axis;
   a first light transmitting optical element connected to the tip having a first end to emit one or more selected wavelengths of light from a first location on the tissue contacting surface and having a second end; and
   a second light transmitting optical element connected to the tip having a first end to receive light corresponding to the one or more selected wavelengths of light at a second location on the tissue contacting surface and having a second end,
   wherein the first and second optical elements are secured to the appliance and the first and second locations are spaced apart, the first optical element first end terminates in the first face in the first plane, and the second optical element first end terminates in the tissue contacting surface;
   a first fixture receiving the second ends of the first and second optical elements;
   a source of light having one or more monochromatic wavelengths;
   a light detector responsive to a sensed light intensity having an electrical signal corresponding to the sensed light intensity;
   a first coupler having a transmission channel input and output and a reception channel input and output, the transmission channel comprising an optical fiber connected to transmit light emitted by the light source to the transmission channel output, the reception channel comprising an optical fiber connected to transmit light coupled to the reception channel input to the light detector, the first coupler being coupled to the first fixture so that the reception channel input is in optical communication with one of the first and second optical elements and the transmission channel output is in optical communication with the other of the first and second optical elements;

a control circuit connected to the light source having a first state to cause the light source to emit light at the one or more wavelengths and said light received at the first end of the other of the first and second optical elements is coupled to the light detector to provide an electrical signal corresponding to said received light; and means for processing the provided electrical signals and determining when the appliance tip is in proximity to venous perfused tissue.

6. The apparatus of claim 5 further comprising an annunciator wherein the processing means actuates the annunciator when the tip is in proximity to venus perfused tissue.

7. The apparatus of claim 6 wherein the processing means further comprises an output signal operable to actuate the annunciator to produce a variable signal corresponding to the extent that the tip has passed in proximity to and into the venus perfused tissue.

8. The apparatus of claim 5 wherein each of the first and second optical elements further comprises a length of fiber optic conductor.

9. A tissue penetrating appliance comprising:

a sharp tip having a tissue contacting surface configured to penetrate tissue and a longitudinal axis, the tissue contacting surface having a first face lying in a first plane at an angle relative to the longitudinal axis;

a first light transmitting optical element connected to the tip having a first end to emit one or more selected wavelengths of light from a first location on the tissue contacting surface and having a second end;

a second light transmitting optical element connected to the tip having a first end to receive light corresponding to the one or more selected wavelengths of light at a second location on the tissue contacting surface and having a second end, wherein the first and second optical elements are secured to the appliance, the first and second locations are spaced apart, the first optical element first end terminates in the first face in the first plane, and the second optical element first end terminates in the tissue contacting surface;

a first fixture receiving the second ends of the first and second optical elements;

a source of light having one or more monochromatic wavelengths;

a light detector responsive to a sensed light intensity having an electrical signal corresponding to the sensed light intensity;

a first coupler having a transmission channel input and output and a reception channel input and output, the transmission channel comprising an optical fiber connected to transmit light emitted by the light source to the transmission channel output, the reception channel comprising an optical fiber connected to transmit light coupled to the reception channel input to the light detector, the first coupler being coupled to the first fixture so that the reception channel input is in optical communication with one of the first and second optical elements and the transmission channel output is in optical communication with the other of the first and second optical elements;

a control circuit connected to the light source having a first state to cause the light source to emit light at the one or more wavelengths and said light received at the first end of the other of the first and second optical elements is coupled to the light detector to provide an electrical signal corresponding to said received light; and means for processing the provided electrical signals and determining when the appliance tip is in proximity to arterial perfused tissue.

10. The apparatus of claim 9 further comprising an annunciator wherein the processing means actuates the annunciator when the tip is in proximity to arterial perfused tissue.

11. The apparatus of claim 10 wherein the processing means further comprises an output signal operable to actuate the annunciator to produce a variable signal corresponding to the extent that the tip has passed in proximity to and into the arterial perfused tissue.

12. The apparatus of claim 9 wherein each of the first and second optical elements further comprises a length of fiber optic conductor.

13. A tissue penetrating appliance comprising:

a sharp tip having a tissue contacting surface configured to penetrate tissue and a longitudinal axis, the tissue contacting surface having a first face lying in a first plane at an angle relative to the longitudinal axis;

a first light transmitting optical element connected to the tip having a first end to emit one or more selected wavelengths of light from a first location on the tissue contacting surface and having a second end;

a second light transmitting optical element connected to the tip having a first end to receive light corresponding to the one or more selected wavelengths of light at a second location on the tissue contacting surface and having a second end, wherein the first and second optical elements are secured to the appliance, and the first and second locations are spaced apart, the first optical element first end terminates in the first face in the first plane, and the second optical element first end terminates in the tissue contacting surface;

a first fixture receiving the second ends of the first and second optical elements;

a first plurality of monochromatic light sources having different discrete wavelengths;

a light detector responsive to a sensed light intensity having an electrical signal corresponding to the sensed light intensity;

a first coupler having a transmission channel input and output and a reception channel input and output, a synchronous optical multiplexer having a plurality of inputs, a plurality of optical fibers respectively connected between the first plurality of monochromatic light sources and the plurality of inputs, and an output to the transmission channel, the reception channel comprising an optical fiber connected to transmit light coupled to the reception channel input to the light detector, the first coupler being coupled to the first fixture so that the reception channel input is in optical communication with one of the first and second optical elements and the transmission channel output is in optical communication with the other of the first and second optical elements;

a control circuit operatively connected to the first plurality of light sources having a first state to cause the first plurality of monochromatic light sources to emit light one at a time in a selected sequence and said light received at the first end of the other of the first and second optical elements is coupled to the light detector to provide an electrical signal corresponding to said received light.

14. The apparatus of claim 13 wherein the first coupler transmission channel further comprises a second light detector optically coupled to the light transmitted to the output of the transmission channel, the second light detector monitoring the intensity of the light emitted at each of the monochromatic wavelengths.

15. The apparatus of claim 13 further comprising a demultiplexer circuit connected to separate the electrical signal provided by the light detector in response to one or more of the monochromatic wavelengths into separate signals corresponding to the one or more monochromatic wavelengths.

16. The apparatus of claim 13 further comprising means for processing the provided electrical signals and determining when the appliance tip has entered a body cavity.

17. The apparatus of claim 13 further comprising means for processing the provided electrical signals and determining when the appliance tip is in proximity to venous perfused tissue.

18. The apparatus of claim 13 further comprising means for processing the provided electrical signals and determining when the appliance tip is in proximity to arterial perfused tissue.

19. The apparatus of claim 13 wherein each of the first and second optical elements further comprises a length of fiber optic conductor.

20. A tissue penetrating appliance comprising:

a sharp tip having a tissue contacting surface configured to penetrate tissue and a longitudinal axis, the tissue contacting surface having a first face lying in a first plane at an angle relative to the longitudinal axis;

a first light transmitting optical element connected to the tip having a first end to emit one or more selected wavelengths of light from a first location on the tissue contacting surface and having a second end;

a second light transmitting optical element connected to the tip having a first end to receive light corresponding to the one or more selected wavelengths of light at a second location on the tissue contacting surface and having a second end, wherein the first and second optical elements are secured to the appliance and the first and second locations are spaced apart, the first optical element first end terminates in the first face in the first plane, and the second optical element first end terminates in the tissue contacting surface;

a first fixture receiving the second ends of the first and second optical elements;

a source of light having one or more monochromatic wavelengths;

a light detector responsive to a sensed light intensity having an electrical signal corresponding to the sensed light intensity;

a first coupler having a transmission channel input and output and a reception channel input and output, the transmission channel comprising an optical fiber connected to transmit light emitted by the light source to the transmission channel output, the reception channel comprising an optical fiber connected to transmit light coupled to the reception channel input to the light detector, the first coupler being coupled to the first fixture so that the reception channel input is in optical communication with one of the first and second optical elements and the transmission channel output is in optical communication with the other of the first and second optical elements;

a control circuit connected to the light source having a first state to cause the light source to emit light at the one or more wavelengths and said light received at the first end of the other of the first and second optical elements is coupled to the light detector to provide an electrical signal corresponding to said received light;

wherein:

the light source further comprises a first plurality of monochromatic light sources having different discrete wavelengths;

the first coupler further comprises:

a wavelength optical multiplexer having a plurality of inputs, a plurality of optical fibers respectively connected between the first plurality of monochromatic light sources and the plurality of inputs; and an output to the transmission channel; wherein the light detector further comprises:

an optical demultiplexer having an input and a plurality of outputs, the input being optically connected to the reception channel, the plurality of outputs corresponding to each of the plurality of monochromatic light sources, a plurality of light detectors, and a plurality of optical fibers coupling the plurality of outputs to the plurality of light detectors;

and wherein the control circuit causes the first plurality of monochromatic light sources to emit light simultaneously and the plurality of light detectors simultaneously provide separate signals corresponding to the received light in response to the discrete wavelengths at the tip.

21. The apparatus of claim 20 further comprising means for processing the provided electrical signals and determining when the appliance tip has entered a body cavity.

22. The apparatus of claim 20 further comprising means for processing the provided electrical signals and determining when the appliance tip is in proximity to venus perfused tissue.

23. The apparatus of claim 20 further comprising means for processing the provided electrical signals and determining when the appliance tip is in proximity to arterial perfused tissue.

24. The apparatus of claim 20 wherein each of the first and second optical elements further comprises a length of fiber optic conductor.

25. A tissue penetrating appliance comprising:

a sharp tip having a longitudinal axis and a tissue contacting surface configured to penetrate tissue including a first face lying in a first plane at an angle relative to the longitudinal axis and a second face in a second plane at an angle relative to the longitudinal axis of the tip, wherein the first and second planes intersect;

a first light transmitting optical element connected to the tip having a first end to emit one or more selected wavelengths of light from a first location on the tissue contacting surface and having a second end, the first optical element first end terminating in the first face in the first plane;

a second light transmitting optical element connected to the tip having a first end to receive light corresponding to the one or more selected wavelengths of light at a second location on the tissue contacting surface and having a second end, the second optical element first end terminating in the second face of the second plane; and a first fixture receiving the second ends of the first and second optical elements.

26. The apparatus of claim 25 wherein the first fixture further comprises:

a pair of optical fibers each having a first end and a second end and a selected length;

a first connector optically connected between the second ends of first and second optical fibers and the first ends of the pair of optical fibers respectively; and a second connector optically connected to the second ends of the pair of optical fibers.

27. The apparatus of claim 20 further comprising:

a source of light having one or more monochromatic wavelengths;

a light detector responsive to a sensed light intensity having an electrical signal corresponding to the sensed light intensity;

a first coupler having a transmission channel input and output and a reception channel input and output, the transmission channel comprising an optical fiber connected to transmit light emitted by the light source to the transmission channel output, the reception channel comprising an optical fiber connected to transmit light coupled to the reception channel input to the light detector, the first coupler coupled to the first fixture so that the reception channel input is in optical communication with one of the first and second optical elements and the transmission channel output is in optical communication with the other of the first and second optical elements; and a control circuit connected to the light source having a first state to cause the light source to emit light at the one or more wavelengths and said light received at the first end of the other of the first and second optical element is coupled to the light detector to provide an electrical signal corresponding to said received light.

28. The apparatus of claim 27 wherein the control circuit further comprises control means for operating the light source to emit light at an intensity, in response to the control circuit being in the first state, whereby the electrical signal includes received light illumination in response to one or more of the monochromatic wavelengths of light emitted.

29. The apparatus of claim 27 wherein each of the first and second optical elements further comprises a length of fiber optic conductor.

30. The apparatus of claim 25 wherein the first end of the second optical element terminates in the first face of the first plane.

31. The apparatus of claim 30 wherein the tissue penetrating appliance is a needle.

32. The apparatus of claim 30 wherein the first face is a conical surface.

33. The apparatus of claim 25 wherein the tip has a longitudinal axis, the tissue contacting surface includes a face lying in a plane inclined relative to the longitudinal axis, and wherein the first optical element first end terminates a first distance below the plane and wherein the second optical element first end terminates a second distance below the tissue contacting surface.

34. The apparatus of claim 25 wherein each of the first and second optical elements further comprises a length of fiber optic conductor.

35. A method for penetrating tissue comprising the steps of:

providing a surgical appliance having a sharp tip having a surface for contacting and penetrating tissue, a first optical element in the tissue contacting surface for emitting one or more selected monochromatic wavelengths of light, and a second optical element in the tissue contacting surface for sensing light corresponding to the one or more selected monochromatic wavelengths of light characterized by securing the first and second optical elements to the tip at locations on the tissue contacting surface spaced a distance apart;

bringing the sharp tip tissue contacting surface into penetrating contact with tissue;

launching light at the one or more selected wavelengths out the first optical element to illuminate tissue;

sensing the light intensity at the second optical element in response to the launched light;

detecting variations in sensed light intensity; an determining when the light intensity variations correspond to the sharp tip passing into and through tissue, wherein the step of detecting variations in light intensity further comprises sensing arterial pulsatile flow in the tissue proximate to the sharp tip.

36. The method of claim 35 wherein the first optical element further comprises a first optical fiber having a first end at the tissue contacting surface and the step of launching light further comprises coupling light from a first light source into the first optical fiber for transmission to the tissue.

37. The method of claim 36 wherein the second optical element further comprises a a second optical fiber having an end at the tissue contacting surface and the step of sensing the light intensity further comprises transmitting the light intensity at the end of the second optical fiber to a light detector.

38. The method of claim 35 further comprising providing an annunciator, detecting when the determined changes in intensity correspond to the tip passing through the tissue approaching a sensed arterial pulsatile flow, and providing a first alarm in response thereto.

39. A method for penetrating tissue comprising the steps of:

providing a surgical appliance having a sharp tip having a surface for contacting and penetrating tissue, a first optical element in the tissue contacting surface for emitting one or more selected monochromatic wavelengths of light, and a second optical element in the tissue contacting surface for sensing light corresponding to the one or more selected monochromatic wavelengths of light characterized by securing the first and second optical elements to the tip at locations on the tissue contacting surface spaced a distance apart;

bringing the sharp tip tissue contacting surface into penetrating contact with tissue;

launching light at the one or more selected wavelengths out the first optical element to illuminate tissue;

sensing the light intensity at the second optical element in response to the launched light;

detecting variations in sensed light intensity; and determining when the light intensity variations correspond to the sharp tip passing into and through tissue;

wherein the first optical element further comprises a first optical fiber having an end at the tissue contacting surface an the step of launching light further comprises coupling light from a first light source into the first optical fiber for transmission to the tissue and wherein the first light source further comprises more than one monochromatic light source and the step of coupling light from the first light source further comprises multiplexing the more than one wavelengths of light into the first optical fiber.

40. The method of claim 39 wherein the second optical element further comprises a a second optical fiber having an end at the tissue contacting surface, the step of launching the light further comprises launching the one or more wavelengths simultaneously, and the step of sensing the light intensity further comprises transmitting the light intensity at the end of the second optical fiber to a light demultiplexor for separating the more than one sensed wavelengths into a corresponding more than one separate optical signals, and separately sensing the light intensity of the wavelength of each separate optical signal.

41. The method of claim 40 wherein the separate signals are separated by wavelength and the step of separately sensing the separate signals further comprises sensing each of the separate signals by a different light detector.

42. The method of claim 39 wherein the first optical element further comprises a first optical fiber having an end at the tissue contacting surface and the step of launching light further comprises coupling light from a first light source into the first optical fiber for transmission to the tissue.

43. The method of claim 42 wherein the second optical element further comprises a second optical fiber having an end at the tissue contacting surface and the step of sensing the light intensity further comprises transmitting the light intensity at the end of the second optical fiber to a light detector.

44. A method for passing a surgical appliance through tissue and into a body cavity comprising:

providing the surgical appliance with a controlled light source and a light detector;

sensing the light intensity at the appliance in response to the controlled light source illumination of the tissue;

generating an electrical signal representative of the sensed light intensity of light at the appliance;

processing the electrical signal to identify changes in sensed light intensity corresponding to the surgical appliance moving relative to the tissue;

identifying a relative change in sensed light intensity based on comparing a first sensed light intensity of the appliance at a first tissue depth and a second sensed light intensity of the appliance at a second tissue depth, the second tissue depth being closer to the body cavity than the first tissue depth; and indicating that the appliance is about to pass into the body cavity in response to the identified relative change corresponding to a selected relative change in light intensity.

45. The method of claim 44 wherein the controlled light source provides more than one monochromatic wavelength of light and the processing and indicating steps further comprise providing separate electrical signals for each of the more than one wavelengths of light sensed, processing each of the provided separate signals separately, and indicating that the appliance is about to pass through the tissue into the body cavity when relative change in intensity of at least one of the one or more separate signals corresponds to a selected relative change in light intensity, each wavelength having a selected relative change appropriate for that wavelength.

46. The method of claim 45 wherein the indicating step further comprises indicating that the appliance is about to pass through the tissue into the body cavity when the relative change in intensity of all of the one or more separate signals corresponds to their respective selected relative changes in light intensity.

47. The method of claim 46 wherein the indicating step further comprises providing a first alarm when the relative intensity change of at least one of the separate signals corresponds to the appliance being about to pass through the tissue into the body cavity and providing a second alarm when the relative intensity changes of all of the separate signals corresponds to the appliance being about to pass through the tissue into the body cavity.

48. The method of claim 45 wherein the indicating step further comprises providing a first alarm.

49. The method of claim 44 wherein the indicating step further comprises providing a first alarm.

50. A method for passing a surgical appliance through tissue comprising:

providing the surgical appliance with a controlled light source and a light detector;

sensing the light intensity at the appliance in response to the controlled light source illumination of the tissue;

generating an electrical signal representative of the sensed light intensity of light at the appliance;

processing the electrical signal to identify changes in sensed light intensity corresponding to the surgical appliance moving relative to the tissue, said processing step comprising evaluating the electrical signal for the existence of sensed light variations corresponding to a blood flow in a blood vessel in the illuminated tissue; and indicating when the appliance is about to pass through a blood vessel in the tissue in response to an identified change of said sensed light variations corresponding to a selected relative change indicative of blood flow.

51. The method of claim 50 wherein the indicating step further comprises indicating when the appliance is about to pass through an venus blood vessel in the tissue.

52. The method of claim 50 wherein the indicating step further comprises indicating when the appliance is about to pass through a venus blood vessel in the tissue.

53. The method of claim 50 wherein the controlled light source provides more than one monochromatic wavelength of light and the processing and indicating steps further comprise providing separate electrical signals for each of the more than one wavelengths of light sensed, processing each of the provided separate signals separately, and indicating that the appliance is about to pass through the blood vessel when the relative change of said sensed light variations of at least one of the one or more separate signals corresponds to a selected relative change indicative of blood flow, each wavelength having a selected relative change appropriate for that wavelength.

54. The method of claim 53 wherein the indicating step further comprises indicating that the appliance has passed into the blood vessel when the relative change in intensity of all of the one or more separate signals corresponds to their respective selected relative changes.

55. The method of claim 50 wherein the indicating step further comprises providing a first alarm.

56. A tissue penetrating appliance comprising:

a sharp tip having a tissue contacting surface configured to penetrate tissue and a longitudinal axis, the tissue contacting surface having a first face lying in a first plane at an angle relative to the longitudinal axis;

a source of light having one or more monochromatic wavelengths;

a light detector responsive to a sensed light intensity having an electrical signal corresponding to the sensed light intensity;

a first light transmitting optical element having a first end and a second end, operatively connected between the light source and the tip to emit from a first location on the tissue contacting surface one or more selected wavelengths of light from the light source;

a second light transmitting optical element having a first end and a second end, operatively connected between the light detector and the tip to receive at a second location on the tissue contacting surface light corresponding to the one or more selected wavelengths of light, the first and second locations being spaced apart, wherein the first optical element first end terminates in the first face in the first plane, and the second optical element first end terminates in the tissue contacting surface;

a control circuit connected to the light source having a first state to cause the light source to emit light at the one or more wavelengths and said light received at the second optical element first end is coupled to the light detector to provide an electrical signal corresponding to said received light; and means for processing the provided electrical signals and determining when the appliance tip has entered a body cavity.

57. The apparatus of claim 56 further comprising means for processing the provided electrical signals and determining when the appliance tip is about to enter a body cavity.

58. The apparatus of claim 57 further comprising an annunciator having a variable audible signal, wherein the processing means actuates the annunciator when the tip is in proximity to the body cavity to produce a variable signal corresponding to the extent that the tip is about to pass into and has passed into the body cavity.

59. The apparatus of claim 56 further comprising means for processing the provided electrical signals and determining when the appliance tip is in proximity to venous perfused tissue.

60. The apparatus of claim 56 further comprising means for processing the provided electrical signals and determining when the appliance tip is in proximity to arterial perfused tissue.

61. The apparatus of claim 56 wherein each of the first and second optical elements further comprises a length of fiber optic conductor.

\* \* \* \* \*

UNITED STATES PATENT AND TRADEMARK OFFICE
CERTIFICATE OF CORRECTION

PATENT NO. : 5,460,182

DATED : October 24, 1995

INVENTOR(S) : David E. Goodman, et. al.

It is certified that error appears in the above-indentified patent and that said Letters Patent is hereby corrected as shown below:

Column 5, line 6, delete "10";

Column 8, line 39, delete "proximate" and insert --proximal--;

Column 10, line 50, delete "e" and insert --"$\alpha$"--;

Column 27, line 45, delete "element" and insert --elements--;

Signed and Sealed this

Twenty-sixth Day of August, 1997

Attest:

BRUCE LEHMAN

*Attesting Officer*   *Commissioner of Patents and Trademarks*